United States Patent
Yamaoka et al.

(12)

(10) Patent No.: US 6,680,366 B1
(45) Date of Patent: *Jan. 20, 2004

(54) NUCLEOTIDE SEQUENCE ENCODING A MODULATOR OF NF-κB

(75) Inventors: Shoji Yamaoka, Paris (FR); Gilles Courtois, Paris (FR); Alain Israel, Paris (FR); Robert Weil, Saint-Clous (FR)

(73) Assignee: Institut Pasteur, Paris (FR)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/253,701

(22) Filed: Feb. 22, 1999

(51) Int. Cl.$^7$ ................... C07K 14/00; C07K 7/00; A61K 38/00
(52) U.S. Cl. ................... 530/350; 530/300; 514/2
(58) Field of Search ................. 530/350, 300; 514/2

(56) References Cited

PUBLICATIONS

Mikayama T. Molecular cloning and functional expression of a cDNA encoding glycosylation–inhibiting factor. Proc. Natl. Acad. Sci. USA vol. 90, pp. 10056–10060, 1993.*

Voet et al. Biochemistry. 1990. John Wiley & Sons, Inc.. pp. 126–128 and 228–234.*

Beers and Berkow eds. The Merck Manual of Diagnosis and Therapy. Seventeenth Edition. Merck Research Laboratories, Whitehouse Station, N. J., 1999, pp. 986–995.*

Beers and Berkow eds. The Merck Manual of Diagnosis and Therapy. Seventeenth Edition. Merck Research Laboratories, Whitehouse Station, N. J., 1999, pp. 986–995.*

Voet et al. Biochemistry. 1990. John Wiley & Sons, Inc.. pp. 126–128 and 228–234.*

* cited by examiner

*Primary Examiner*—Yvonne Eyler
*Assistant Examiner*—Joseph F. Murphy
(74) *Attorney, Agent, or Firm*—Oblon, Spivak, McClelland, Maier & Neustadt, P.C.

(57) ABSTRACT

The present invention relates to nucleotide sequences encoding a modulator of NF-κB, and to the polypeptides encoded by the nucleotide sequences. In particular, the invention relates to nucleotide sequences and the polypeptides encoded thereby, wherein the polypeptides are involved in the response to NF-κB-activating stimuli, including HTLV-1 Tax, LPS, PMA and IL-1. The invention also relates to antibodies to the modulator of NF-κB, methods of detecting modulator of NF-κB using the antibodies, methods of treatment associated with NF-κB activation and to methods of identifying compounds which modulate the activity of the modulator of NF-κB.

4 Claims, 13 Drawing Sheets

```
1
MNKHPWKNQLSETVQPSGGPAEDQDMLGEESSLGKPAMLHLPSEQGTPET    50

LQRCLEENQELRDAIRQSNQMLRERCEELLHFQVSQREEKEFLMCKFQEA    100

RKLVERLSLEKLDLRSQREQALKELEQLKKCQQQMAEDKASVKAQVTSLL    150

GELQESQSRLEAATKDRQALEGRIRAVSEQVRQLESEREVLQQQHSVQVD    200

QLRMQNQSVEAALRMERQAASEEKRKLAQLQAAYHQLFQDYDSHIKSSKG    250

MQLEDLRQQLQQAEEALVAKQELIDKLKEEAEQHKIVMETVPVLKAQADI    300

YKADFQAERHAREKLVEKKEYLQEQLEQLQREFNKLKVGCHESARIEIMR    350

KRHVETPQPPLLPAPAHHSFHLALSNQRRSPPEEPPDFCCPKCQYQAPDM    400

DTLQIHVMECI                                         412
```

FIG. 3 rNEMO —→

```
ACCGCGGTGGCGGCCGCTCTAGAACTAGTGGATCCCTCTGCTCCTGCCCT
CTTCACTTCTGGCCGACTCTGCTGACAGACACTGTCCTGTTGGATGAACA
AGCACCCCTGGAAGAACCAGCTGAGTGAGACGGTGCAGCCCAGTGGTGGC
CCAGCAGAGGACCAGGACATGCTGGGTGAAGAATCTTCTCTGGGGAAGCC
TGCAATGCTACATCTGCCTTCAGAGCAGGGTACTCCTGAGACCCTCCAGC
GCTGCCTGGAAGAGAATCAAGAGCTCCGAGACGCTATCCGGCAGAGCAAT
CAGATGCTGAGGGAACGCTGTGAGGAGCTGCTGCATTTCCAGGTCAGCCA
GCGGGAGGAGAAGGAGTTCCTTATGTGCAAATTCCAGGAAGCCCGGAAGC
TGGTGGAGAGACTGAGCTTGGAGAAGCTTGATCTTCGGAGTCAGAGGGAA
CAGGCCTTAAAGGAGTTGGAGCAACTGAAGAAATGCCAACAGCAGATGGC
TGAGGACAAGGCCTCTGTGAAAGCTCAGGTGACATCATTGCTCGGAGAAC
TCCAGGAGAGCCAGAGCCGTTTGGAGGCTGCCACCAAGGATCGGCAAGCT
TTAGAGGGAAGGATTCGAGCAGTTAGTGAGCAGGTCAGACAGCTGGAGAG
TGAGCGGGAGGTGCTACAGCAGCAGCACAGCGTCCAGGTGGACCAGCTGC
GTATGCAGAACCAGAGCGTGGAGGCTGCCTTGCGAATGGAGCGGCAGGCT
GCTTCAGAGGAGAAGCGGAAGCTGGCTCAGTTGCAGGCAGCCTATCACCA
ACTCTTCCAAGACTACGACAGCCACATTAAGAGCAGCAAGGGCATGCAGC
TGGAAGATCTGAGGCAACAGCTCCAGCAAGCTGAGGAGGCCCTGGTAGCC
AAACAGGAATTGATTGATAAGCTGAAAGAGGAGGCTGAGCAGCACAAGAT
TGTGATGGAGACTGTGCCAGTCTTGAAGGCCCAGGCGGATATCTACAAGG
CTGACTTCCAAGCTGAGAGGCATGCCCGGGAGAAGCTGGTGGAGAAGAAG
GAGTATTTGCAGGAGCAGCTGGAGCAGCTGCAGCGCGAGTTCAACAAGCT
GAAAGTTGGCTGCCATGAGTCAGCCAGGATTGAGGATATGAGGAAGCGGC
ATGTAGAGACTCCCCAGCCTCCTTTACTCCCTGCTCCAGCTCACCACTCC
TTTCATTTGGCCTTGTCCAACCAGCGGAGGAGCCCTCCTGAAGAACCTCC
TGACTTCTGTTGTCCGAAGTGCCAGTATCAGGCTCCTGATATGGACACTC
TACAGATACATGTCATGGAGTGCATAGAGTAGGAGCAGCAGATGCAAGGC
CACTTGCAGTACTATGTCCTGATCTGTGTGACTTGTGCTTTCCTGTTTTA
CCTGCATAGTCCACACTTAAGGGCTTGCTTTAGCCCTTTGGTCCCCCATT
TAGGGTAGACAGCCCCATTCAGGGCTTTTTTTTTTTTTCTGTGTGCCTGAT
CCAGTTTGCCTCTGGTGGCTTCTTCCCTCTTCTCCCATAGTCCTAGGGAG
TCTAGAATGGAGGCCAGGGGCTCTTAGGGAGCATCCCTTCTCCAAGCAGG
TCTGGGTACAGCTTTTCTTCTCTCCAACTGGTACCTTTCTTGCCGGTGAA
CTGCAGGCTCTCCTCCCAGGGCATGTGGCACTTGGGTCTATAACATGTGT
TACCTCTGGTAGACATGTGGAAAGTATTCTGTCCTTTTGTTACTGTAATT
AATGGTGTAGTGAAAGTACTTGTACACTGATCTGTGTGTACCTTTAGGAC
AGATGCTTAGATGTGACATTGGATCCCCCGGGCTGCAGGAATTCGATATC
AAGCTTATCGATACCGTCGACCTC
```

FIG.8

SEQUENCE LISTING

```
<160> NUMBER OF SEQ ID NOS:   3

<210> SEQ ID NO 1
<211> LENGTH: 411
<212> TYPE: PRT
<213> ORGANISM: Homo sapiens

<400> SEQUENCE: 1

Met Asn Lys Lys His Pro Trp Lys Asn Gln Leu Ser Glu Thr Val Gln
1               5                   10                  15
```

```
Pro Ser Gly Gly Pro Ala Glu Asp Gln Asp Met Leu Gly Glu Ser
         20                  25                  30
Ser Leu Gly Lys Pro Ala Met Leu His Leu Pro Ser Glu Gln Gly Thr
     35                  40                  45
Pro Glu Thr Leu Gln Arg Cys Leu Glu Glu Asn Gln Glu Leu Arg Asp
 50                  55                  60
Ala Ile Arg Gln Ser Asn Gln Met Leu Arg Glu Arg Cys Glu Glu Leu
65                  70                  75                  80
Leu His Phe Gln Val Ser Gln Arg Glu Glu Lys Glu Phe Leu Met Cys
                 85                  90                  95
Lys Phe Gln Glu Ala Arg Lys Leu Val Glu Arg Leu Ser Leu Glu Lys
             100                 105                 110
Leu Asp Leu Arg Ser Gln Arg Glu Gln Ala Leu Lys Glu Leu Glu Gln
         115                 120                 125
Leu Lys Lys Cys Gln Gln Met Ala Glu Asp Lys Ala Ser Val Lys
     130                 135                 140
Ala Gln Val Thr Ser Leu Leu Gly Glu Leu Gln Glu Ser Gln Ser Arg
145                 150                 155                 160
Leu Glu Ala Ala Thr Lys Asp Arg Gln Ala Leu Glu Gly Arg Ile Arg
                 165                 170                 175
Ala Val Ser Glu Gln Val Arg Gln Leu Glu Ser Glu Arg Glu Val Leu
             180                 185                 190
Gln Gln Gln His Ser Val Gln Val Asp Gln Leu Arg Met Gln Asn Gln
         195                 200                 205
Ser Val Glu Ala Ala Leu Arg Met Glu Arg Gln Ala Ala Ser Glu Glu
     210                 215                 220
Lys Arg Lys Leu Ala Gln Leu Gln Ala Ala Tyr His Gln Leu Phe Gln
225                 230                 235                 240
Asp Tyr Asp Ser His Ile Lys Ser Ser Lys Gly Met Gln Leu Glu Asp
                 245                 250                 255
Leu Arg Gln Gln Leu Gln Gln Ala Glu Glu Ala Leu Val Ala Lys Gln
             260                 265                 270
Glu Leu Ile Asp Lys Leu Lys Glu Glu Ala Glu Gln His Lys Ile Val
         275                 280                 285
Met Glu Thr Val Pro Val Leu Lys Ala Gln Ala Asp Ile Tyr Lys Ala
     290                 295                 300
Asp Phe Gln Ala Glu Arg His Ala Arg Glu Lys Leu Val Glu Lys Lys
305                 310                 315                 320
Glu Tyr Leu Gln Glu Gln Leu Glu Gln Leu Gln Arg Glu Phe Asn Lys
                 325                 330                 335
Leu Lys Val Gly Cys Cys His Glu Ser Ala Arg Ile Glu Asp Met Arg
             340                 345                 350
Lys Arg His Val Glu Thr Pro Gln Pro Leu Leu Pro Ala Pro Ala
         355                 360                 365
His His Ser Phe His Leu Ala Leu Ser Asn Gln Arg Arg Ser Pro Pro
     370                 375                 380
Glu Glu Pro Asp Phe Cys Cys Pro Lys Cys Gln Tyr Gln Ala Pro Asp
385                 390                 395                 400
Met Asp Thr Gln Ile His Val Met Glu Cys Ile
                 405                 410

<210> SEQ ID NO 2
<211> LENGTH: 1874
```

<212> TYPE: DNA
<213> ORGANISM: Homo sapiens

<400> SEQUENCE: 2

```
accgcggtgg cggccgctct agaactagtg gatccctctg ctcctgccct cttcacttct      60
ggccgactct gctgacagac actgtcctgt tggatgaaca agcacccctg gaagaaccag     120
ctgagtgaga cggtgcagcc cagtggtggc ccagcagagg accaggacat gctgggtgaa     180
gaatcttctc tggggaagcc tgcaatgcta catctgcctt cagagcaggg tactcctgag     240
accctccagc gctgcctgga agagaatcaa gagctccgag acgctatccg gcagagcaat     300
cagatgctga gggaacgctg tgaggagctg ctgcatttcc aggtcagcca gcgggaggag     360
aaggagttcc ttatgtgcaa attccaggaa gcccggaagc tggtggagag actgagcttg     420
gagaagcttg atcttcggag tcagagggaa caggccttaa aggagttgga gcaactgaag     480
aaatgccaac agcagatggc tgaggacaag gcctctgtga agctcaggt gacatcattg      540
ctcggagaac tccaggagag ccagagccgt ttggaggctg ccaccaagga tcggcaagct     600
ttagagggaa ggattcgagc agttagtgag caggtcagac agctggagag tgagcgggag     660
gtgctacagc agcagcacag cgtccaggtg gaccagctgc gtatgcagaa ccagagcgtg     720
gaggctgcct tgcgaatgga gcggcaggct gcttcagagg agaagcggaa gctggctcag     780
ttgcaggcag cctatcacca actcttccaa gactacgaca gccacattaa gagcagcaag     840
ggcatgcagc tggaagatct gaggcaacag ctccagcaag ctgaggaggc cctggtagcc     900
aaacaggaat tgattgataa gctgaaagag gaggctgagc agcacaagat tgtgatggag     960
actgtgccag tcttgaaggc ccaggcggat atctacaagg ctgacttcca agctgagagg    1020
catgcccggg agaagctggt ggagaagaag gagtatttgc aggagcagct ggagcagctg    1080
cagcgcgagt tcaacaagct gaaagttggc tgccatgagt cagccaggat tgaggatatg    1140
aggaagcggc atgtagagac tccccagcct cctttactcc ctgctccagc tcaccactcc    1200
tttcatttgg ccttgtccaa ccagcggagg agccctcctg aagaacctcc tgacttctgt    1260
tgtccgaagt gccagtatca ggctcctgat atggacactc tacagataca tgtcatggag    1320
tgcatagagt aggagcagca gatgcaaggc cacttgcagt actatgtcct gatctgtgtg    1380
acttgtgctt tcctgtttta cctgcatagt ccacacttaa gggcttgctt tagccctttg    1440
gtcccccatt tagggtagac agccccattc agggcttttt ttttttttctg tgtgcctgat    1500
ccagtttgcc tctggtggct tcttccctct tctcccatag tcctagggag tctagaatgg    1560
aggccagggg ctcttaggga gcatcccttc tccaagcagg tctgggtaca gcttttcttc    1620
tctccaactg gtacctttct tgccggtgaa ctgcaggctc tcctcccagg gcatgtggca    1680
cttgggtcta taacatgtgt tacctctggt agacatgtgg aaagtattct gtccttttgt    1740
tactgtaatt aatggtgtag tgaaagtact tgtacactga tctgtgtgta cctttaggac    1800
agatgcttag atgtgacatt ggatcccccg ggctgcagga attcgatatc aagcttatcg    1860
ataccgtcga cctc                                                      1874
```

<210> SEQ ID NO 3
<211> LENGTH: 19
<212> TYPE: DNA
<213> ORGANISM: Artificial/Unknown
<220> FEATURE:
<221> NAME/KEY: misc_feature
<222> LOCATION: ()..()
<223> OTHER INFORMATION: Description of Artificial Sequence: primer

```
                                            -continued

<400> SEQUENCE: 3
tcagagggga ctttccgag                                                    19
```

NUCLEOTIDE SEQUENCE ENCODING A MODULATOR OF NF-κB

BACKGROUND OF THE INVENTION

1. Field of the Invention

The present invention relates to nucleotide sequences encoding a modulator of NF-κB, and to the polypeptides encoded by the nucleotide sequences. In particular, the invention relates to nucleotide sequences and the polypeptides encoded thereby, wherein the polypeptides are involved in the response to NF-κB activating stimuli, including HTLV-I Tax, LPS, PMA and IL-1.

2. Discussion of the Background

The Rel/NF-κB family of transcription factors plays important roles in immune and stress responses, in inflammation, in apoptosis, and regulates the expression of numerous cellular and viral genes (for recent reviews, see Baldwin, 1996; Verma et al., 1995; May and Ghosh, 1998). The NF-κB activity is composed of homo- or heterodimers of related proteins that share a conserved DNA-binding and dimerization domain called the Rel Homology Domain. In most cell types, NF-κB is sequestered in the cytoplasm bound to inhibitory proteins called IκB-α, IκB-β and IκB-ε. In response to diverse stimuli, including inflammatory cytokines, mitogens, bacterial lipopolysaccharide (LPS), or some viral products, active NF-κB is released and translocated to the nucleus as a result of the proteolytic degradation of IκB proteins. Phosphorylation of IκBα on Ser 32 and 36 targets the molecule for degradation by the ubiquitin-26S proteasome pathway. While the processes leading to the degradation of the IκB proteins are relatively well understood, the mechanism by which a variety of distinct signals initiated from the cell membrane are transduced to their common targets, the IκB proteins, remains to be elucidated. A protein kinase activity was identified as a large multisubunit complex which can phosphorylate IκBα at Ser 32 and 36 (Chen et al., 1996; Lee et al., 1997). Most recently, two related kinases have been cloned which contain a catalytic domain at the amino-terminus and a leucine zipper (LZ) as well as a helix-loop helix (HLH) motif at the carboxy terminus (Didonato et al., 1997; Mercurio et al., 1997; Regnier et al., 1997; Woronicz et al., 1997; Zandi et al., 1997). Although both of them have been shown to be essential contributors to cytokine-mediated NF-κB activation, understanding of the precise nature of the IκB kinase activity and its regulatory mechanisms needed further investigation and identification of the other subunits of the kinase complex. Another important issue unanswered was how discrete activation signals triggered by a variety of known stimulators are integrated to give rise to IκB kinase activity.

One attractive approach to such questions would be the use of somatic cell genetics. Although the diploidy of the mammalian genome presents a major hurdle to a genetic approach, successful establishment of recessive mutants has provided helpful information on a signaling pathway and a reliable way to identify relevant gene(s) by complementation. Indeed, the Janus kinase family of tyrosine kinases was identified as essential signal transducers for the interferons through a genetic approach (Darnell et al., 1994; Velazquez et al., 1992). Concerning the NF-κB signaling pathways, the characterization of a mutant of the murine pre-B cell line 70Z/3, 1.3E2, has previously been reported, which had been isolated by selecting cells unable to express surface IgM following lipopolysaccharide stimulation (Courtois et al., 1997).

The recent description of a high molecular weight cytoplasmic complex able to phosphorylate IκBα on serines 32 and 36 (Chen et al., 1996; Lee et al., 1997) has prompted intense studies, which culminated a few months ago with the cloning of two kinases, named IKK-1 and IKK-2, or IKKα and IKKβ (Didonato et al., 1997; Mercurio et al., 1997; Regnier et al., 1997; Woronicz et al., 1997; Zandi et al., 1997). Two approaches were used to this end: one involved biochemical purification from a cytoplasmic extract derived from TNF-treated HeLa cells (Didonato et al., 1997; Mercurio et al., 1997; Zandi et al., 1997), while the other used a 2-hybrid screen using as a bait NIK, a protein kinase previously shown to be involved in TNF- and IL-1-induced NF-κB activation (Regnier et al., 1997; Woronicz et al., 1997). The cloned kinases were postulated to directly phosphorylate serines 32 and 36 of IκBα, although this has not been formally demonstrated. The reason for this uncertainty is that all kinase assays reported so far rely on immunoprecipitation of transfected or in vitro translated IKK, therefore leaving open the possibility that the "true" IκB kinase is coprecipitated together with IKK and the rest of the high molecular weight complex. Immunoprecipitation of one kinase from extracts of cells transfected with the two kinases results in the coprecipitation of the second kinase, and a more detailed study has demonstrated that heteroassociation was favored over homo-association. The sequence of IKK-1 and IKK-2 has revealed two interesting features: a leucine zipper and a helix-loop-helix motif. Deletion of the LZ in one of the kinases results in the abrogation of coimmunoprecipitation with either itself or the other kinase, and a strong reduction in the resulting kinase activity. However it is unclear whether the LZ motif is required for direct interaction between the kinase subunits or between the kinase(s) and some other component of the complex. Deletion of the HLH motif leaves the coimmunoprecipitation of the two kinases intact, but strongly reduces the resulting kinase activity. In the assays used in the above mentioned papers, transfected IKK-2 seems to exhibit a stronger basal kinase activity when compared to IKK-1 (Mercurio et al., 1997; Zandi et al., 1997). Zandi et al. (Zandi et al., 1997) also observed that cotranslation of the two kinases in wheat germ extracts resulted in no IκB kinase activity, suggesting that either post-translational modifications or additional components of the complex (or both) are required. Cotranslation of the two kinases in wheat germ extracts precluded their association. One possibility is that the kinase subunits need to be incorporated into the 600–800 kD complex in order to be fully active, and that some critical components of the complex are absent in wheat germ extracts. In any case all these data emphasize the importance of identifying additional components of the complex.

If the identity of molecules involved in NF-κB activation were known, one could block NF-κB activation, and thereby treat cellular dysfunctions associated therewith, by inactivating these molecules.

In view of the aforementioned limited information regarding molecules involved in NF-κB activation, it is clear that there exists a need in the art for identifying the sequences encoding such molecules.

SUMMARY OF THE INVENTION

Accordingly, one object of this invention is to provide a modulator of NF-κB and its subunits in purified form that exhibits certain characteristics and activities associated with inhibition of NF-κB activity.

It is a further object of the present invention to provide antibodies to the modulator of NF-κB and its subunits, and methods for their preparation, including recombinant means.

It is a further object of the present invention to provide a method for detecting the presence of the modulator of NF-κB and its subunits in mammals in which invasive, spontaneous, or idiopathic pathological states are suspected to be present.

It is a further object of the present invention to provide a method and associated assay system for screening substances such as drugs, agents and the like, potentially effective in either mimicking the activity or fighting against the adverse effects of the modulator of NF-κB and/or its subunits in mammals.

It is a still further object of the present invention to provide a method for the treatment of mammals to control the transcriptional activity induced by NF-κB, so as to alter the adverse consequences of such presence or activity, or where beneficial, to enhance such activity.

It is a still further object of the present invention to provide a method for the treatment of mammals to control the amount or activity of the transcriptional activity of NF-κB, so as to treat or avert the adverse consequences of invasive, spontaneous or idiopathic pathological states.

It is a still further object of the present invention to provide pharmaceutical compositions for use in therapeutic methods which comprise or are based upon the modulator of NF-κB, its subunits, their binding partner(s), or upon agents or drugs that control the production, or that mimic or antagonize the activities of the modulator of NF-κB.

With the foregoing and other objects, advantages and features of the invention that will become hereinafter apparent, the nature of the invention may be more clearly understood by reference to the following detailed description of the preferred embodiments of the invention and to the appended claims.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

Figure 1A:
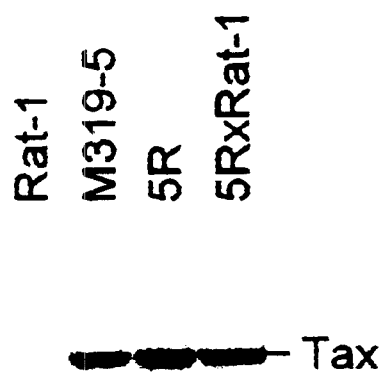
FIG. 1. Characterisation of 5R cells. A. Fifty pg of whole cell extracts derived from wild-type Rat-1 cells (lane 1), the Tax-transformed clone M319-5 (lane 2), the 5R flat revertant (lane 3) and a pool of hybrids between 5R and a Rat-1 derived clone bearing an integrated hygromycin resistance gene (lane 4) were analyzed by immunoblotting using anti Tax mAb M173.

B. Five μg of nuclear extracts derived from the same cells (as indicated above the lanes) were analyzed by bandshift assay using the κB site derived from the H-2K$^b$ promoter as a probe. The NF-κB complex is indicated by a square dot on the right. C, D. Rat-1 or 5R cells were cotransfected with 0.25 μg of HTLV-1 LTR-luciferase (panel C) or IgK-luciferase (panel D) and 1 μg of either empty vector (C) or Tax or relA expression vectors. Luciferase activity was measured after 40 hours. Fold induction over basal level is shown.

E. Rat-1 or 5R cells (as indicated) were co-cultured with Rat-1 cells carrying an integrated Igκ-luciferase plasmid, treated with (+) or without (−) 50% PEG for 1 minute and harvested 12 hours later. Equivalent amount of protein extract was used for the luciferase assay.

FIG. 2. Response of Rat-1 and 5R cells to NF-κB activating signals.

A. Bandshift assay of nuclear extracts from Rat-1 or 5R cells either untreated (nione) or stimulated as indicated above the lanes. Stimulation was for 30 minutes with 10 ng/ml of TNF-α, 20 ng/ml of IL-1, 15 μg/ml of LPS or 0.1 mg/ml of dsRNA.

B. Transactivation of Igκ-luciferase transfected Rat-1 or 5R cells by TNF-α (T), IL-1 (I), LPS (L) or dsRNA (R). Stimulation was for 3 hours.

C. Immunoblotting analysis of extracts derived from LPS treated Rat-1 or 5R cells. Cytoplasmic extracts were prepared at the indicated times and 50 μg analyzed by Western blotting.

FIG. 3. Sequence of the NEMO protein (SEQ ID NO:1). The putative leucine zipper is boxed.

FIG. 4. NEMO complements the defect in 5R cells. A. Rat-1 or 5R cells were transiently transfected with 0.25 μg of Igκ-luciferase and the indicated amount of CMV-hygro-NEMO. Luciferase assays were performed as described in FIG. 2.

B. Band shift assay of Rat-1- or 5R-derived cell lines stably expressing NEMO. Five μg of nuclear extracts derived from the following cell lines were analyzed as in FIG. 1. Lane 1: wild-type Rat-1 cells. Lane 2: a pool of Rat-1 cells transfected with CMV-hygro-NEMO. Lane 3: 5R cells. Lane 4: h12 cells (5R cells containing the inducible blasticidin S resistance gene). Lanes 5, 6: cDNA library infected h12 clones that survived the blasticidin S selection. The size of the cDNA amplified from each clone is indicated. Lanes 7, 8: Independent pools of 5R cells stably transfected with CMV-hygro-NEMO. Lanes 9, 10: two representative 5R cell clones obtained by stable transfection with CMV-hygro-NEMO.

C. Immunoblotting analysis of cytoplasmic extracts (100 μg) derived from Rat-1 or 5R cells was carried out with an antibody specific for NEMO. rNEMO: rat NEMO.

FIG. 5. NEMO complements the defect in 1.3E2 cells. A. 1.3E2, 1.3E2 stably transfected with NEMO (1.3E2N) and 70Z/3 cells were transiently cotransfected with 3 μg of Igκ-luciferase and 6 μg of CMV-hygro-NEMO. After 24 hours, cells were splitted in two and left untreated (−) or stimulated (+) with 15 μg/ml LPS. Luciferase assays were performed as described in FIG. 2.

B. Bandshift assay of complemented 1.3E2 cells. 70Z/3 (lanes 1–4), 1.3E2 (lanes 5–8) or a pool of 1.3E2 cells stably transfected with CMV-hygro-NEMO (1.3E2N, lanes 9–12) were left untreated (lanes 12, 5 9), or stimulated with 15 μg/ml LPS (lanes 2, 6, 10), 100 ng/ml PMA (lanes 3, 7, 11) or 20 ng/ml IL-1 (lanes 4, 8, 12). Five μg of nuclear extracts were then analyzed by bandshift using the H-2 K$^b$ derived κB site.

C. Immunoblotting analysis of cytoplasmic extracts (100 μg) derived from 70Z/3 or 1.3E2 cells was carried out with the NEMO antiserum. mNEMO: mouse NEMO.

Figure 6:
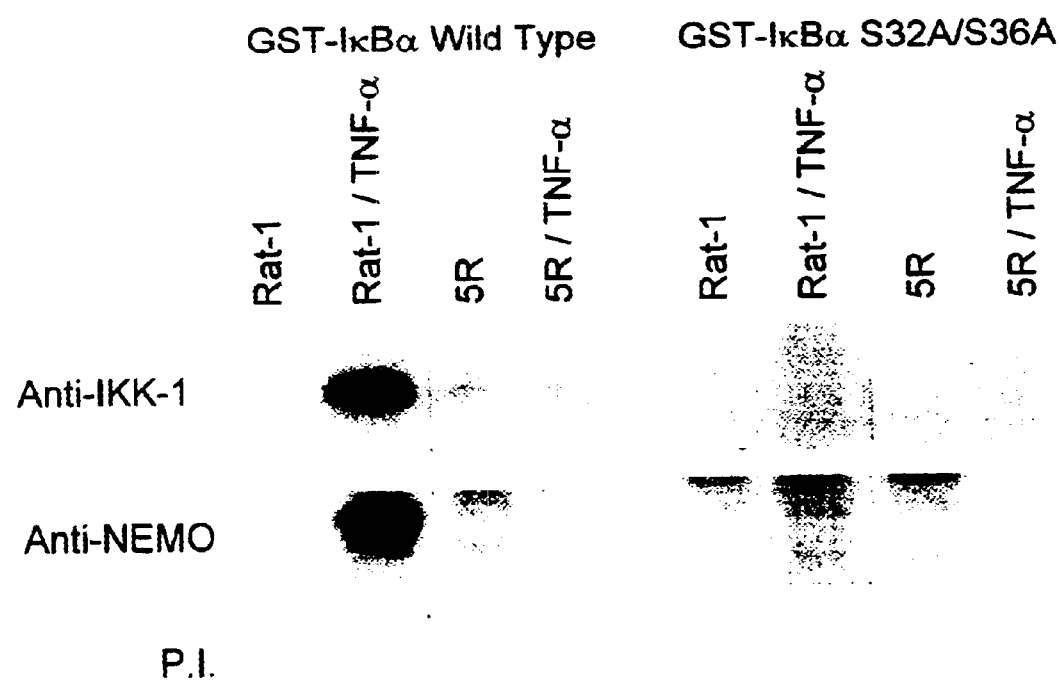

FIG. 6. NEMO is associated with an inducible endogenous IκBα kinase activity. Rat-1 or 5R cells were treated for 5 minutes with or without TNF-α (10 ng/ml). Cytoplasmic extracts were immunoprecipitated with either preimmune serum (P.I.), anti-IKK-1 antibody (anti-IKK-1) or NEMO antiserum (anti-NEMO) and specific IκBα kinase activity was determined by an in vitro immune complex kinase assay with GST-IκBα (1–72) wild type or GST-IκBα (1–72) S32A/S36A mutant protein as substrates.

FIG. 7. NEMO is a subunit of the IκB kinase complex A. Gel filtration analysis of NEMO and IκB kinase complex in Rat-1 and 5R cells. S100 extracts were prepared as described in Materials and Methods and fractionated through a Superose 6 column. Fractions were analyzed by Western blotting, using antibodies specific for IKK-1 or NEMO. Analysis of NF-κB/IκB elution, using an anti-relA antibody is also shown. To demonstrate identical elution of Rat-1 and 5R extracts, the protein profile from each fraction was analyzed by silver staining (Upper pannel).

B. Coimmunoprecipitation of IKK-1 with NEMO. Positive NEMO fractions from Rat-1 and the equivalent fractions from 5R cells were imunoprecipitated with anti-NEMO, run through a 7.5% SDS-Laemmli gel and immunoblotted with anti-IKK-1.

C. NEMO forms homodimers. The NEMO protein was in vitro synthesized in wheat germ extract and treated with the indicated concentrations of glutaraldehyde. The reactions were immunoprecipitated with NEMO antiserum and analysed on a 8% SDS-polyacrylamide gel. The positions of the NEMO monomer and NEMO dimer ((NEMO)$_2$) are indicated. Lo; in vitro translated product.

D. In vitro interaction between NEMO and IKK-2. Untagged NEMO (lane 1), VSV-IKK-2 (lane 3), or both molecules (lane 2) were in vitro translated in wheat germ extract (Load). The $^{35}$S labelled products were then precipitated with anti-VSV antibody (VSV-IP). Lane 4 represents unprogrammed wheat germ extract. The relevant proteins are indicated on the right.

FIG. 8. Nucleotide sequence of NEMO (SEQ ID NO:2).

DESCRIPTION OF THE PREFERRED EMBODIMENTS

In accordance with the present invention there may be employed conventional molecular biology, microbiology, and recombinant DNA techniques within the skill of the art. Such techniques are explained fully in the literature. See, e.g., Sambrook et al, "Molecular Cloning: A Laboratory Manual" (1989); "Current Protocols in Molecular Biology" Volumes I–III [Ausubel, R. M., ed. (1994)]; "Cell Biology: A Laboratory Handbook" Volumes I–III [J. E. Celis, ed. (1994))]; "Current Protocols in Immunology" Volumes I–III [Coligan, J. E., ed. (1994)]; "Oligonucleotide Synthesis" (M. J. Gait ed. 1984); "Nucleic Acid Hybridization" [B. D. Hames & S. J. Higgins eds. (1985)]; "Transcription And Translation" [B. D. Hames & S. J. Higgins, eds. (1984)]; "Animal Cell Culture" [R. I. Freshney, ed. (1986)]; "Immobilized Cells And Enzymes" [IRL Press, (1986)]; B. Perbal, "A Practical Guide To Molecular Cloning" (1984).

Therefore, if appearing herein, the following terms shall have the definitions set out below.

The term "modulator of NF-κB" and any variants not specifically listed as used throughout the present application and claims refer to proteinaceous material including single or multiple proteins, and extends to those proteins having the amino acid sequence data described herein and presented in FIG. 3 (SEQ ID NO:1), and the profile of activities set forth herein and in the Claims. Accordingly, proteins displaying substantially equivalent or altered activity are likewise contemplated. These modifications may be deliberate, for example, such as modifications obtained through site-directed mutagenesis, or may be accidental, such as those obtained through mutations in hosts that are producers of the complex or its named subunits. Also, the term "modulator of NF-κB" is intended to include within its scope proteins specifically recited herein as well as all substantially homologous analogs and allelic variations.

The amino acid residues described herein are preferred to be in the "L" isomeric form. However, residues in the "D" isomeric form can be substituted for any L-amino acid residue, as long as the desired functional property of immunoglobulin-binding is retained by the polypeptide. NH$_2$ refers to the free amino group present at the amino terminus of a polypeptide. COOH refers to the free carboxy group present at the carboxy terminus of a polypeptide.

It should be noted that all amino-acid residue sequences are represented herein by formulae whose left and right orientation is in the conventional direction of amino-terminus to carboxy-terminus. Furthermore, it should be noted that a dash at the beginning or end of an amino acid residue sequence indicates a peptide bond to a further sequence of one or more amino-acid residues.

A "replicon" is any genetic element (e.g., plasmid, chromosome, virus) that functions as an autonomous unit of DNA replication in vivo; i.e., capable of replication under its own control.

A "vector" is a replicon, such as plasmid, phage or cosmid, to which another DNA segment may be attached so as to bring about the replication of the attached segment.

A "DNA molecule" refers to the polymeric form of deoxyribonucleotides (adenine, guanine, thymine, or cytosine) in its either single stranded form, or a double-stranded helix. This term refers only to the primary and secondary structure of the molecule, and does not limit it to any particular tertiary forms. Thus, this term includes double-stranded DNA found, inter alia, in linear DNA molecules (e.g., restriction fragments), viruses, plasmids, and chromosomes. In discussing the structure of particular double-stranded DNA molecules, sequences may be described herein according to the normal convention of giving only the sequence in the 5' to 3' direction along the nontranscribed strand of DNA (i.e., the strand having a sequence homologous to the mRNA).

An "origin of replication" refers to those DNA sequences that participate in DNA synthesis.

A DNA "coding sequence" is a double-stranded DNA sequence which is transcribed and translated into a polypeptide in vivo when placed under the control of appropriate regulatory sequences. The boundaries of the coding sequence are determined by a start codon at the 5' (amino) terminus and a translation stop codon at the 3' (carboxyl) terminus. A coding sequence can include, but is not limited to, prokaryotic sequences, cDNA from eukaryotic MRNA, genomic DNA sequences from eukaryotic (e.g., mammalian) DNA, and even synthetic DNA sequences. A polyadenylation signal and transcription termination sequence will usually be located 3' to the coding sequence.

Transcriptional and translational control sequences are DNA regulatory sequences, such as promoters, enhancers, polyadenylation signals, terminators, and the like, that provide for the expression of a coding sequence in a host cell.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined by mapping with nuclease S1), as well as protein binding domains (consensus sequences) responsible for the binding of RNA polymerase. Eukaryotic promoters will often, but not always, contain "TATA" boxes and "CAT" boxes.

Prokaryotic promoters contain Shine-Dalgarno sequences in addition to the −10 and −35 consensus sequences.

An "expression control sequence" is a DNA sequence that controls and regulates the transcription and translation of another DNA sequence. A coding sequence is "under the control" of transcriptional and translational control sequences in a cell when RNA polymerase transcribes the coding sequence into MRNA, which is then translated into the protein encoded by the coding sequence.

A "signal sequence" can be included before the coding sequence. This sequence encodes a signal peptide, N-terminal to the polypeptide, that communicates to the host cell to direct the polypeptide to the cell surface or secrete the polypeptide into the media, and this signal peptide is clipped off by the host cell before the protein leaves the cell. Signal sequences can be found associated with a variety of proteins native to prokaryotes and eukaryotes.

The term "oligonucleotide," as used herein in referring to the probe of the present invention, is defined as a molecule comprised of two or more ribonucleotides, preferably more than three. Its exact size will depend upon many factors which, in turn, depend upon the ultimate function and use of the oligonucleotide.

The term "primer" as used herein refers to an oligonucleotide, whether occurring naturally as in a purified restriction digest or produced synthetically, which is capable of acting as a point of initiation of synthesis when placed under conditions in which synthesis of a primer extension product, which is complementary to a nucleic acid strand, is induced, i.e., in the presence of nucleotides and an inducing agent such as a DNA polymerase and at a suitable temperature and pH. The primer may be either single-stranded or double-stranded and must be sufficiently long to prime the synthesis of the desired extension product in the presence of the inducing agent. The exact length of the primer will depend upon many factors, including temperature, source of primer and use of the method. For example, for diagnostic applications, depending on the complexity of the target sequence, the oligonucleotide primer typically contains 15–25 or more nucleotides, although it may contain fewer nucleotides.

The primers herein are selected to be "substantially" complementary to different strands of a particular target DNA sequence. This means that the primers must be sufficiently complementary to hybridize with their respective strands. Therefore, the primer sequence need not reflect the exact sequence of the template. For example, a non-complementary nucleotide fragment may be attached to the 5' end of the primer, with the remainder of the primer sequence being complementary to the strand. Alternatively, non-complementary bases or longer sequences can be interspersed into the primer, provided that the primer sequence has sufficient complementarity with the sequence of the strand to hybridize therewith and thereby form the template for the synthesis of the extension product.

As used herein, the terms "restriction endonucleases" and "restriction enzymes" refer to bacterial enzymes, each of which cut double-stranded DNA at or near a specific nucleotide sequence.

A cell has been "transformed" by exogenous or heterologous DNA when such DNA has been introduced inside the cell. The transforming DNA may or may not be integrated (covalently linked) into chromosomal DNA making up the genome of the cell. In prokaryotes, yeast, and mammalian cells for example, the transforming DNA may be maintained on an episomal element such as a plasmid. With respect to eukaryotic cells, a stably transformed cell is one in which the transforming DNA has become integrated into a chromosome so that it is inherited by daughter cells through chromosome replication. This stability is demonstrated by the ability of the eukaryotic cell to establish cell lines or clones comprised of a population of daughter cells containing the transforming DNA. A "clone" is a population of cells derived from a single cell or common ancestor by mitosis. A "cell line" is a clone of a primary cell that is capable of stable growth in vitro for many generations.

Two DNA sequences are "substantially homologous" when at least about 75% (preferably at least about 80%, and most preferably at least about 90 or 95%) of the nucleotides match over the defined length of the DNA sequences. Sequences that are substantially homologous can be identified by comparing the sequences using standard software available in sequence data banks, or in a Southern hybridization experiment under, for example, stringent conditions as defined for that particular system. Defining appropriate hybridization conditions is within the skill of the art. See, e.g., Maniatis et al., supra; DNA Cloning, Vols. I & II, supra; Nucleic Acid Hybridization, supra.

It should be appreciated that also within the scope of the present invention are DNA sequences encoding modulators of NF-κB which code for a modulator of NF-κB having the same amino acid sequence as SEQ ID NO:1, but which are degenerate to SEQ ID NO:2. By "degenerate to" is meant that a different three-letter codon is used to specify a particular amino acid. It is well known in the art that the following codons can be used interchangeably to code for each specific amino acid:

| | |
|---|---|
| Phenylalanine (Phe or F) | UUU or UUC |
| Leucine (Leu or L) | UUA or UUG or CUU or CUC or CUA or CUG |
| Isoleucine (Ile or I) | AUU or AUC or AUA |
| Methionine (Met or M) | AUG |
| Valine (Val or V) | GUU or GUC of GUA or GUG |
| Serine (Ser or S) | UCU or UCC or UCA or UCG or AGU or AGC |
| Proline (Pro or P) | CCU or CCC or CCA or CCG |
| Threonine (Thr or T) | ACU or ACC or ACA or ACG |
| Alanine (Ala or A) | GCU or GCG or GCA or GCG |
| Tyrosine (Tyr or Y) | UAU or UAC |
| Histidine (His or H) | CAU or CAC |
| Glutamine (Gln or Q) | CAA or CAG |
| Asparagine (Asn or N) | AAU or AAC |
| Lysine (Lys or K) | AAA or AAG |
| Aspartic Acid (Asp or D) | GAU or GAC |
| Glutamic Acid (Glu or E) | GAA or GAG |
| Cysteine (Cys or C) | UGU or UGC |
| Arginine (Arg or R) | CGU or CGC or CGA or CGG or AGA or AGG |
| Glycine (Gly or G) | GGU or GGC or GGA or GGG |
| Tryptophan (Trp or W) | UGG |
| Termination codon | UAA (ochre) or UAG (amber) or UGA (opal) |

It should be understood that the codons specified above are for RNA sequences. The corresponding codons for DNA have a T substituted for U.

Mutations can be made in SEQ ID NO:2 such that a particular codon is changed to a codon which codes for a different amino acid. Such a mutation is generally made by making the fewest nucleotide changes possible. A substitution mutation of this sort can be made to change an amino acid in the resulting protein in a non-conservative manner (i.e., by changing the codon from an amino acid belonging to a grouping of amino acids having a particular size or characteristic to an amino acid belonging to another grouping) or in a conservative manner (i.e., by changing the codon from an amino acid belonging to a grouping of amino acids having a particular size or characteristic to an amino acid belonging to the same grouping). Such a conservative change generally leads to less change in the structure and function of the resulting protein. A non-conservative change is more likely to alter the structure, activity or function of the resulting protein. The present invention should be considered to include seguences containing conservative changes which do not significantly alter the activity or binding characteristics of the resulting protein.

The following is one example of various groupings of amino acids:
Amino Acids With Nonpolar R Groups
Alanine
Valine
Leucine
Isoleucine
Proline
Phenylalanine
Tryptophan
Methionine
Amino Acids With Uncharged Polar R Groups
Glycine
Serine
Threonine
Cysteine
Tyrosine
Asparagine
Glutamine
Aimino Acids With Charged Polar R Groups (Negatively Charged at Ph 6.0)
Aspartic acid
Glutamic acid
Basic Amino Acids (Positively Charged at pH 6.0)
Lysine
Arginine
Histidine (at pH 6.0)

Another grouping may be those amino acids with phenyl groups:
Phenylalanine
Tryptophan
Tyrosine Another grouping may be according to molecular weight (i.e., size of R groups):

| | |
|---|---|
| Glycine | 75 |
| Alanine | 89 |
| Serine | 105 |
| Proline | 115 |
| Valine | 117 |
| Threonine | 119 |
| Cysteine | 121 |
| Leucine | 131 |
| Isoleucine | 131 |
| Asparagine | 132 |
| Aspartic acid | 133 |
| Glutamine | 146 |
| Lysine | 146 |
| Glutamic acid | 147 |
| Methionine | 149 |
| Histidine (at pH 6.0) | 155 |
| Phenylalanine | 165 |
| Arginine | 174 |
| Tyrosine | 181 |
| Tryptophan | 204 |

Particularly preferred substitutions are:
Lys for Arg and vice versa such that a positive charge may be maintained;

Glu for Asp and vice versa such that a negative charge may be maintained;
Ser for Thr such that a free —OH can be maintained; and
Gln for Asn such that a free $NH_2$ can be maintained.

Amino acid substitutions may also be introduced to substitute an amino acid with a particularly preferable property. For example, a Cys may be introduced a potential site for disulfide bridges with another Cys. A His may be introduced as a particularly "catalytic" site (i.e., His can act as an acid or base and is the most common amino acid in biochemical catalysis). Pro may be introduced because of its particularly planar structure, which induces β-turns in the protein's structure.

Two amino acid sequences are "substantially homologous" when at least about 70% of the amino acid residues (preferably at least about 80%, and most preferably at least about 90 or 95%) are identical, or represent conservative substitutions.

A "heterologous" region of the DNA construct is an identifiable segment of DNA within a larger DNA molecule that is not found in association with the larger molecule in nature. Thus, when the heterologous region encodes a mammalian gene, the gene will usually be flanked by DNA that does not flank the mammalian genomic DNA in the genome of the source organism. Another example of a heterologous coding sequence is a construct where the coding sequence itself is not found in nature (e.g., a cDNA where the genomic coding sequence contains introns, or synthetic sequences having codons different than the native gene). Allelic variations or naturally-occurring mutational events do not give rise to a heterologous region of DNA as defined herein.

An "antibody" is any immunoglobulin, including antibodies and fragments thereof, that binds a specific epitope. The term encompasses polyclonal, monoclonal, and chimeric antibodies, the last mentioned described in further detail in U.S. Pat. Nos. 4,816,397 and 4,816,567.

An "antibody combining site" is that structural portion of an antibody molecule comprised of heavy and light chain variable and hypervariable regions that specifically binds antigen.

The phrase "antibody molecule" in its various grammatical forms as used herein contemplates both an intact immunoglobulin molecule and an immunologically active portion of an immunoglobulin molecule.

Exemplary antibody molecules are intact immunoglobulin molecules, substantially intact immunoglobulin molecules and those portions of an immunoglobulin molecule that contains the paratope, including those portions known in the art as Fab, Fab', F(ab')$_2$ and F(v), which portions are preferred for use in the therapeutic methods described herein.

Fab and F(ab')$_2$ portions of antibody molecules are prepared by the proteolytic reaction of papain and pepsin, respectively, on substantially intact antibody molecules by methods that are well-known. See for example, U.S. Pat. No. 4,342,566 to Theofilopolous et al. Fab'antibody molecule portions are also well-known and are produced from F(ab')$_2$ portions followed by reduction of the disulfide bonds linking the two heavy chain portions as with mercaptoethanol, and followed by alkylation of the resulting protein mercaptan with a reagent such as iodoacetamide. An antibody containing intact antibody molecules is preferred herein.

The phrase "monoclonal antibody" in its various grammatical forms refers to an antibody having only one species of antibody combining site capable of immunoreacting with a particular antigen. A monoclonal antibody thus typically displays a single binding affinity for any antigen with which it immunoreacts. A monoclonal antibody may therefore contain an antibody molecule having a plurality of antibody combining sites, each immunospecific for a different antigen; e.g., a bispecific (chimeric) monoclonal antibody.

The phrase "pharmaceutically acceptable" refers to molecular entities and compositions that are physiologically tolerable and do not typically produce an allergic or similar untoward reaction, such as gastric upset, dizziness and the like, when administered to a human.

The phrase "therapeutically effective amount" is used herein to mean an amount sufficient to prevent, and preferably reduce by at least about 30 percent, more preferably by at least 50 percent, most preferably by at least 90 percent, a clinically significant change in the S phase activity of a target cellular mass, or other feature of pathology such as for example, elevated blood pressure, fever or white cell count as may attend its presence and activity.

A DNA sequence is "operatively linked" to an expression control sequence when the expression control sequence controls and regulates the transcription and translation of that DNA sequence. The term "operatively linked" includes having an appropriate start signal (e.g., ATG) in front of the DNA sequence to be expressed and maintaining the correct reading frame to permit expression of the DNA sequence under the control of the expression control sequence and production of the desired product encoded by the DNA sequence. If a gene that one desires to insert into a recombinant DNA molecule does not contain an appropriate start signal, such a start signal can be inserted in front of the gene.

The term "standard hybridization conditions" refers to salt and temperature conditions substantially equivalent to 5×SSC and 65° C. for both hybridization and wash. However, one skilled in the art will appreciate that such "standard hybridization conditions" are dependent on particular conditions including the concentration of sodium and magnesium in the buffer, nucleotide sequence length and concentration, percent mismatch, percent formamide, and the like. Also important in the determination of "standard hybridization conditions" is whether the two sequences hybridizing are RNA-RNA, DNA-DNA or RNA-DNA. Such standard hybridization conditions are easily determined by one skilled in the art according to well known formulae, wherein hybridization is typically 10–20° C. below the predicted or determined $T_m$ with washes of higher stringency, if desired.

In its primary aspect, the present invention concerns the identification of a modulator of NF-κB.

In a particular embodiment, the present invention relates to a modulator of NF-κB termed NF-κB Essential Modulator (NEMO)

As stated above, the present invention also relates to a recombinant DNA molecule or cloned gene, or a degenerate variant thereof, which encodes a modulator of NF-κB, or a fragment thereof, that possesses a molecular weight of about 48 kD and an amino acid sequence set forth in FIG. 3 (SEQ ID NO:1); preferably a nucleic acid molecule, in particular a recombinant DNA molecule or cloned gene, encoding the 48 kD modulator of NF-κB has a nucleotide sequence or is complementary to a DNA sequence shown in FIG. 8 (SEQ ID NO:2).

The possibilities both diagnostic and therapeutic that are raised by the existence of the modulator of NF-κB, derive from the fact that this modulator appears to participate in direct and causal protein-protein interaction with at least one of the IκB kinases, which is involved in the activation of NF-κB. As suggested earlier and elaborated further on herein, the present invention contemplates pharmaceutical intervention in the cascade of reactions in which the modulator of NF-κB is implicated, to modulate the activity initiated by the modulator of NF-κB.

Thus, in instances where it is desired to reduce or inhibit the modulator of NF-κB resulting from a particular stimulus or factor, an appropriate inhibitor of the modulator of NF-κB could be introduced to block the interaction of the modulator of NF-κB with those factors to which the modulator of NF-κB binds (e.g., the IκB kinase). Correspondingly, instances where insufficient NF-κB-induced transcriptional activity is taking place could be remedied by the introduction of additional quantities of the modulator of NF-κB or its chemical or pharmaceutical cognates, analogs, fragments and the like.

As discussed earlier, the modulator of NF-κB or its binding partners or other ligands or agents exhibiting either mimicry or antagonism to the modulator of NF-κB or control over its production, may be prepared in pharmaceutical compositions, with a suitable carrier and at a strength effective for administration by various means to a patient experiencing an adverse medical condition associated with NF-κB activation for the treatment thereof. A variety of administrative techniques may be utilized, among them parenteral techniques such as subcutaneous, intravenous and intraperitoneal injections, catheterizations and the like. Average quantities of the modulator of NF-κB or its subunits may vary and in particular should be based upon the recommendations and prescription of a qualified physician or veterinarian.

Also, antibodies including both polyclonal and monoclonal antibodies, and drugs that modulate the production or activity of the modulator of NF-κB and/or its subunits may possess certain diagnostic applications and may for example, be utilized for the purpose of detecting and/or measuring conditions such as viral infection or the like. For example, the modulator of NF-κB or its subunits may be used to produce both polyclonal and monoclonal antibodies to themselves in a variety of cellular media, by known techniques such as the hybridoma technique utilizing, for example, fused mouse spleen lymphocytes and myeloma cells. Likewise, small molecules that mimic or antagonize the activity(ies) of the modulator of NF-κB of the invention may be discovered or synthesized, and may be used in diagnostic and/or therapeutic protocols.

The general methodology for making monoclonal antibodies by hybridomas is well known. Immortal, antibody-producing cell lines can also be created by techniques other than fusion, such as direct transformation of B lymphocytes with oncogenic DNA, or transfection with Epstein-Barr virus. See, e.g., M. Schreier et al., "Hybridoma Techniques" (1980); Hammerling et al., "Monoclonal Antibodies And T-cell Hybridomas" (1981); Kennett et al., "Monoclonal Antibodies" (1980); see also U.S. Pat. Nos. 4,341,761; 4,399,121; 4,427,783; 4,444,887; 4,451,570; 4,466,917; 4,472,500; 4,491,632; 4,493,890.

Panels of monoclonal antibodies produced against modulator of NF-κB peptides can be screened for various properties; i.e., isotype, epitope, affinity, etc. Of particular interest are monoclonal antibodies that neutralize the activity of the modulator of NF-κB or its subunits. High affinity antibodies are also useful when immunoaffinity purification of native or recombinant modulator of NF-κB is possible.

Preferably, the anti-NF-κB modulator antibody used in the diagnostic methods of this invention is an affinity purified polyclonal antibody. More preferably, the antibody is a monoclonal antibody (niAb). In addition, it is preferable for the anti-NF-κB modulator antibody molecules used herein be in the form of Fab', Fab', F(ab')₂ or F(v) portions of whole antibody molecules.

Methods for producing polyclonal anti-polypeptide antibodies are well-known in the art. See U.S. Pat. No. 4,493,795 to Nestor et al. A monoclonal antibody, typically containing Fab and/or F(ab')₂ portions of useful antibody molecules, can be prepared using the hybridoma technology described in *Antibodies—A Laboratory Manual*, Harlow and Lane, eds., Cold Spring Harbor Laboratory, New York (1988), which is incorporated herein by reference. Briefly, to form the hybridoma from which the monoclonal antibody composition is produced, a myeloma or other self-perpetuating cell line is fused with lymphocytes obtained from the spleen of a mammal hyperimmunized with a NF-κB modulator-binding portion thereof, or NF-κB modulator.

Splenocytes are typically fused with myeloma cells using polyethylene glycol (PEG) 6000. Fused hybrids are selected by their sensitivity to HAT. Hybridomas producing a monoclonal antibody useful in practicing this invention are identified by their ability to immunoreact with the present NF-κB modulator.

A monoclonal antibody useful in practicing the present invention can be produced by initiating a monoclonal hybridoma culture comprising a nutrient medium containing a hybridoma that secretes antibody molecules of the appropriate antigen specificity. The culture is maintained under conditions and for a time period sufficient for the hybridoma to secrete the antibody molecules into the medium. The antibody-containing medium is then collected. The antibody molecules can then be further isolated by well-known techniques.

Media useful for the preparation of these compositions are both well-known in the art and commercially available and include synthetic culture media, inbred mice and the like. An exemplary synthetic medium is Dulbecco's minimal essential medium (DMEM; Dulbecco et al., *Virol.* 8:396 (1959)) supplemented with 4.5 gm/I glucose, 20 mm glutamine, and 20% fetal calf serum. An exemplary inbred mouse strain is the Balb/c.

Methods for producing monoclonal anti-NF-κB modulator antibodies are also well-known in the art. See Niman et al., *Proc. Natl. Acad. Sci. USA*, 80:4949–4953 (1983). Typically, the present NF-κB modulator or a peptide analog is used either alone or conjugated to an immunogenic carrier, as the immunogen in the before described procedure for producing anti-NF-κB modulator monoclonal antibodies. The hybridomas are screened for the ability to produce an antibody that immunoreacts with the NF-κB modulator peptide analog and the present NF-κB modulator.

The present invention further contemplates therapeutic compositions useful in practicing the therapeutic methods of this invention. A subject therapeutic composition includes, in admixture, a pharmaceutically acceptable excipient (carrier) and one or more of a NF-κB modulator, polypeptide analog thereof or fragment thereof, as described herein as an active ingredient. In a preferred embodiment, the composition comprises an antigen capable of modulating the specific binding of the present NF-κB modulator within a target cell.

The preparation of therapeutic compositions which contain polypeptides, analogs or active fragments as active ingredients is well understood in the art. Typically, such compositions are prepared as injectables, either as liquid solutions or suspensions, however, solid forms suitable for solution in, or suspension in, liquid prior to injection can also be prepared. The preparation can also be emulsified. The active therapeutic ingredient is often mixed with excipients which are pharmaceutically acceptable and compatible with the active ingredient. Suitable excipients are, for example, water, saline, dextrose, glycerol, ethanol, or the like and combinations thereof. In addition, if desired, the composition can contain minor amounts of auxiliary substances such as wetting or emulsifying agents, pH buffering agents which enhance the effectiveness of the active ingredient.

A polypeptide, analog or active fragment can be formulated into the therapeutic composition as neutralized pharmaceutically acceptable salt forms. Pharmaceutically acceptable salts include the acid addition salts (formed with the free amino groups of the polypeptide or antibody molecule) and which are formed with inorganic acids such as, for example, hydrochloric or phosphoric acids, or such organic acids as acetic, oxalic, tartaric, mandelic, and the like. Salts formed from the free carboxyl groups can also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

The therapeutic polypeptide-, analog- or active fragment-containing compositions are conventionally administered intravenously, as by injection of a unit dose, for example. The term "unit dose" when used in reference to a therapeutic composition of the present invention refers to physically discrete units suitable as unitary dosage for humans, each unit containing a predetermined quantity of active material calculated to produce the desired therapeutic effect in association with the required diluent; i.e., carrier, or vehicle.

The present invention also relates to a recombinant DNA molecule or cloned gene, or a degenerate variant thereof, which encodes a NF-κB modulator; preferably a nucleic acid molecule, in particular a recombinant DNA molecule or cloned gene, encoding the NF-κB modulator has a nucleotide sequence or is complementary to a DNA sequence shown in FIG. 8 (SEQ ID NO:2).

The human and murine DNA sequences of the NF-κB modulator of the present invention or portions thereof, may be prepared as probes to screen for complementary sequences and genomic clones in the same or alternate species. The present invention extends to probes so prepared that may be provided for screening cDNA and genomic libraries for the NF-κB modulator. For example, the probes may be prepared with a variety of known vectors, such as the phage λ vector. The present invention also includes the preparation of plasmids including such vectors, and the use of the DNA sequences to construct vectors expressing antisense RNA or ribozymes which would attack the mRNAs of the DNA sequence set forth in FIG. 8 (SEQ ID NO:2). Correspondingly, the preparation of antisense RNA and ribozymes are included herein.

The present invention also includes NF-κB modulator proteins having the activities noted herein, and that display the amino acid sequences set forth and described above and having SEQ ID NO:1.

In a further embodiment of the invention, the full DNA sequence of the recombinant DNA molecule or cloned gene so determined may be operatively linked to an expression control sequence which may be introduced into an appropriate host. The invention accordingly extends to unicellular hosts transformed with the cloned gene or recombinant DNA molecule comprising a DNA sequence encoding the present NF-RB modulator(s), and more particularly, the complete DNA sequence determined from the sequences set forth above and in SEQ ID NO:2.

According to other preferred features of certain preferred embodiments of the present invention, a recombinant expression system is provided to produce biologically active animal or human NF-κB modulator.

The concept of the NF-κB modulator contemplates that specific factors exist for correspondingly specific ligands, such as the IκB kinase and the like, as described earlier. Accordingly, the exact structure of each NF-κB modulator will understandably vary so as to achieve this ligand and activity specificity. It is this specificity and the direct involvement of the NF-κB modulator in the chain of events leading to NF-κB-1 induced transcriptional activity, that offers the promise of a broad spectrum of diagnostic and therapeutic utilities.

The present invention naturally contemplates several means for preparation of the NF-κB modulator, including as illustrated herein known recombinant techniques, and the invention is accordingly intended to cover such synthetic preparations within its scope. The isolation of the cDNA and amino acid sequences disclosed herein facilitates the reproduction of the NF-κB modulator by such recombinant techniques, and accordingly, the invention extends to expression vectors prepared from the disclosed DNA sequences for expression in host systems by recombinant DNA techniques, and to the resulting transformed hosts.

The invention includes an assay system for screening of potential drugs effective to modulate NF-κB modulator activity of target mammalian cells by interrupting or potentiating the nuclear translocation of NF-κB. In one instance, the test drug could be administered to a cellular sample, to determine its effect upon the binding activity of the NF-κB modulator to any chemical sample (including the IκB kinase), or to the test drug, by comparison with a control.

The assay system could more importantly be adapted to identify drugs or other entities that are capable of binding to the NF-κB modulator, thereby inhibiting or potentiating NF-κB-1 induced transcriptional activity. Such assay would be useful in the development of drugs that would be specific against particular cellular activity, or that would potentiate such activity, in time or in level of activity. For example, such drugs might be used to modulate immune responses, stress responses, inflammation or apoptosis, or to treat other pathologies, as for example, viral infection.

In yet a further embodiment, the invention contemplates antagonists of the activity of a NF-κB modulator.

The present invention likewise extends to the development of antibodies against the NF-κB modulator(s), including naturally raised and recombinantly prepared antibodies. For example, the antibodies could be used to screen expression libraries to obtain the gene or genes that encode the NF-κB modulator(s). Such antibodies could include both polyclonal and monoclonal antibodies prepared by known genetic techniques, as well as bi-specific (chimeric) antibodies, and antibodies including other functionalities suiting them for additional diagnostic use conjunctive with their capability of modulating NF-κB activity.

Thus, the NF-κB modulator, its analogs, and any antagonists or antibodies that may be raised thereto, are capable of use in connection with various diagnostic techniques, including immunoassays, such as a radioimmunoassay, using for example, an antibody to the NF-κB modulator that has been labeled by either radioactive addition, or radioiodination.

In an immunoassay, a control quantity of the antagonists or antibodies thereto, or the like may be prepared and labeled with an enzyme, a specific binding partner and/or a radioactive element, and may then be introduced into a cellular sample. After the labeled material or its binding partner(s) has had an opportunity to react with sites within the sample, the resulting mass may be examined by known techniques, which may vary with the nature of the label attached.

In the instance where a radioactive label, such as the isotopes $^{3}$H, $^{14}$C, $^{32}$P, 35S, $^{36}$Cl, $^{51}$Cr, $^{57}$Co, $^{58}$Co, $^{59}$Fe, $^{90}$Y, $^{125}$I, $^{131}$I, and $^{186}$Re are used, known currently available counting procedures may be utilized. In the instance where the label is an enzyme, detection may be accomplished by any of the presently utilized calorimetric, spectrophotometric, fluorospectrophotometric, amperometric or gasometric techniques known in the art.

The present invention includes an assay system which may be prepared in the form of a test kit for the quantitative analysis of the extent of the presence of the NF-κB modulator, or to identify drugs or other agents that may mimic or block its activity. The system or test kit may comprise a labeled component prepared by one of the radioactive and/or enzymatic techniques discussed herein, coupling a label to the NF-κB modulator, its agonists and/or antagonists, and one or more additional immunochemical reagents, at least one of which is a free or immobilized ligand, capable either of binding with the labeled component, its binding partner, one of the components to be determined or their binding partner(s).

In a further embodiment, the present invention relates to certain therapeutic methods which would be based upon the activity of the NF-κB modulator(s), its subunits, or active fragments thereof, or upon agents or other drugs determined to possess the same activity. A first therapeutic method is associated with the prevention of the manifestations of conditions causally related to or following from the nuclear translocation of NF-κB, and comprises administering an agent capable of modulating the production and/or activity of the NF-κB modulator or subunits thereof, either individually or in mixture with each other in an amount effective to prevent the development of those conditions in the host. For example, drugs or other binding partners to the NF-κB modulator or proteins may be administered to inhibit or potentiate NF-κB activity.

More specifically, the therapeutic method generally referred to herein could include the method for the treatment of various pathologies or other cellular dysfunctions and derangements by the administration of pharmaceutical compositions that may comprise effective inhibitors or enhancers of activation of the NF-κB modulator or its subunits, or other equally effective drugs developed for instance by a drug screening assay prepared and used in accordance with a further aspect of the present invention. For example, drugs or other binding partners to the NF-κB modulator, as represented by SEQ ID NO:1, may be administered to inhibit or potentiate NF-κB-1 induced transcriptional activity.

Another feature of this invention is the expression of the DNA sequences disclosed herein. As is well known in the art, DNA sequences may be expressed by operatively linking them to an expression control sequence in an appropriate expression vector and employing that expression vector to transform an appropriate unicellular host.

Such operative linking of a DNA sequence of this invention to an expression control sequence, of course, includes, if not already part of the DNA sequence, the provision of an initiation codon, ATG, in the correct reading frame upstream of the DNA sequence.

A wide variety of host/expression vector combinations may be employed in expressing the DNA sequences of this invention. Useful expression vectors, for example, may consist of segments of chromosomal, non-chromosomal and synthetic DNA sequences. Suitable vectors include derivatives of SV40 and known bacterial plasmids, e.g., *E. coli* plasmids col E1, pCR1, pBR322, pMB9 and their derivatives, plasmids such as RP4; phage DNAS, e.g., the numerous derivatives of phage λ, e.g., NM989, and other phage DNA, e.g., M13 and filamentous single stranded phage DNA; yeast plasmids such as the 2μ plasmid or derivatives thereof; vectors useful in eukaryotic cells, such as vectors useful in insect or mammalian cells; vectors derived from combinations of plasmids and phage DNAs, such as plasmids that have been modified to employ phage DNA or other expression control sequences; and the like.

Any of a wide variety of expression control sequences—sequences that control the expression of a DNA sequence operatively linked to it—may be used in these vectors to express the DNA sequences of this invention. Such useful expression control sequences include, for example, the early or late promoters of SV40, CMV, vaccinia, polyoma or adenovirus, the lac system, the trp system, the TAC system, the TRC system, the LYR system, the major operator and promoter regions of phage λ, the control regions of fd coat protein, the promoter for 3-phosphoglycerate kinase or other glycolytic enzymes, the promoters of acid phosphatase (e.g., Pho5), the promoters of the yeast α-mating factors, and other sequences known to control the expression of genes of prokaryotic or eukaryotic cells or their viruses, and various combinations thereof.

A wide variety of unicellular host cells are also useful in expressing the DNA sequences of this invention. These hosts may include well known eukaryotic and prokaryotic hosts, such as strains of *E. coli*, Pseudomonas, Bacillus, Streptomyces, fungi such as yeasts, and animal cells, such as CHO, R1.1, B-W and L-M cells, African Green Monkey kidney cells (e.g., COS 1, COS 7, BSC1, BSC40, and BMT10), insect cells (e.g., Sf9), and human cells and plant cells in tissue culture.

It will be understood that not all vectors, expression control sequences and hosts will function equally well to express the DNA sequences of this invention. Neither will all hosts function equally well with the same expression system. However, one skilled in the art will be able to select the proper vectors, expression control sequences, and hosts without undue experimentation to accomplish the desired expression without departing from the scope of this invention. For example, in selecting a vector, the host must be considered because the vector must function in it. The vector's copy number, the ability to control that copy number, and the expression of any other proteins encoded by the vector, such as antibiotic markers, will also be considered.

In selecting an expression control sequence, a variety of factors will normally be considered. These include, for example, the relative strength of the system, its controllability, and its compatibility with the particular DNA sequence or gene to be expressed, particularly as regards potential secondary structures. Suitable unicellular hosts will be selected by consideration of, e.g., their compatibility with the chosen vector, their secretion characteristics, their ability to fold proteins correctly, and their fermentation requirements, as well as the toxicity to the host of the product encoded by the DNA sequences to be expressed, and the ease of purification of the expression products.

Considering these and other factors a person skilled in the art will be able to construct a variety of vector/expression control sequence/host combinations that will express the DNA sequences of this invention on fermentation or in large scale animal culture.

It is further intended that NF-κB modulator analogs may be prepared from nucleotide sequences of the protein complex/subunit derived within the scope of the present invention. Analogs, such as fragments, may be produced, for example, by pepsin digestion of NF-κB modulator material. Other analogs, such as muteins, can be produced by standard site-directed mutagenesis of NF-κB modulator coding sequences. Analogs exhibiting "NF-κB modulator activity" such as small molecules, whether functioning as promoters or inhibitors, may be identified by known in vivo and/or in vitro assays.

As mentioned above, a DNA sequence encoding NF-κB modulator can be prepared synthetically rather than cloned. The DNA sequence can be designed with the appropriate codons for the NF-κB modulator amino acid sequence. In general, one will select preferred codons for the intended host if the sequence will be used for expression. The complete sequence is assembled from overlapping oligonucleotides prepared by standard methods and assembled into a complete coding sequence. See, e.g., Edge, *Nature*, 292:756 (1981); Nambair et al., *Science*, 223:1299 (1984); Jay et al., *J. Biol. Chem.*, 259:6311 (1984).

Synthetic DNA sequences allow convenient construction of genes which will express NF-κB modulator analogs or "muteins". Alternatively, DNA encoding muteins can be made by site-directed mutagenesis of native NF-κB modulator genes or cDNAs, and muteins can be made directly using conventional polypeptide synthesis.

A general method for site-specific incorporation of unnatural amino acids into proteins is described in Christopher J. Noren, Spencer J. Anthony-Cahill, Michael C. Griffith, Peter G. Schultz, *Science*, 244:182–188 (April 1989). This method may be used to create analogs with unnatural amino acids.

The present invention extends to the preparation of antisense oligonucleotides and ribozymes that may be used to interfere with the expression of the NF-κB modulator at the translational level. This approach utilizes antisense nucleic acid and ribozymes to block translation of a specific MRNA, either by masking that mRNA with an antisense nucleic acid or cleaving it with a ribozyme.

Antisense nucleic acids are DNA or RNA molecules that are complementary to at least a portion of a specific mRNA molecule. (See Weintraub, 1990; Marcus-Sekura, 1988.) In the cell, they hybridize to that mRNA, forming a double stranded molecule. The cell does not translate an MRNA in this double-stranded form. Therefore, antisense nucleic acids interfere with the expression of mRNA into protein. Oligomers of about fifteen nucleotides and molecules that hybridize to the AUG initiation codon will be particularly efficient, since they are easy to synthesize and are likely to pose fewer problems than larger molecules when introducing them into NF-κB modulator-producing cells. Antisense methods have been used to inhibit the expression of many genes in vitro (Marcus-Sekura, 1988; Hambor et al., 1988).

Ribozymes are RNA molecules possessing the ability to specifically cleave other single stranded RNA molecules in a manner somewhat analogous to DNA restriction endonucleases. Ribozymes were discovered from the observation that certain mRNAs have the ability to excise their own introns. By modifying the nucleotide sequence of these RNAs, researchers have been able to engineer molecules that recognize specific nucleotide sequences in an RNA molecule and cleave it (Cech, 1988.). Because they are sequence-specific, only mRNAs with particular sequences are inactivated.

Investigators have identified two types of ribozymes, Tetrahymena-type and "hammerhead"-type. (Hasselhoff and Gerlach, 1988) Tetrahymena-type ribozymes recognize four-base sequences, while "hammerhead"-type recognize eleven- to eighteen-base sequences. The longer the recognition sequence, the more likely it is to occur exclusively in the target mRNA species. Therefore, hammerhead-type ribozymes are preferable to Tetrahymena-type ribozymes for inactivating a specific MRNA species, and eighteen base recognition sequences are preferable to shorter recognition sequences.

The DNA sequences described herein may thus be used to prepare antisense molecules against, and ribozymes that cleave mRNAs for NF-κB modulator and its ligands.

The present invention also relates to a variety of diagnostic applications, including methods for detecting the presence of stimuli such as the earlier referenced polypeptide ligands, by reference to their ability to elicit the activities which are mediated by the present NF-κB modulator. As mentioned earlier, the NF-κB modulator can be used to produce antibodies to itself by a variety of known techniques, and such antibodies could then be isolated and utilized as in tests for the presence of particular NF-κB modulator activity in suspect target cells.

As described in detail above, antibody(ies) to the NF-κB modulator can be produced and isolated by standard methods including the well known hybridoma techniques. For convenience, the antibody(ies) to the NF-κB modulator will be referred to herein as $Ab_1$ and antibody(ies) raised in another species as $Ab_2$.

The presence of NF-κB modulator in cells can be ascertained by the usual immunological procedures applicable to such determinations. A number of useful procedures are known. Three such procedures which are especially useful utilize either the NF-κB modulator labeled with a detectable label, antibody $Ab_1$ labeled with a detectable label, or antibody $Ab_2$ labeled with a detectable label. The procedures may be summarized by the following equations wherein the asterisk indicates that the particle is labeled, and "NF-κBM" stands for the NF-κB modulator:

$$NF\text{-}\kappa BM^* + Ab = NF\text{-}\kappa BM^* Ab_1 \qquad \text{A.}$$

$$NF\text{-}\kappa BM + Ab^* = NF\text{-}\kappa BM\ Ab_1^*. \qquad \text{B.}$$

$$NF\text{-}\kappa BM + Ab_1 + Ab_2^* = NF\text{-}\kappa BM\ Ab_1 Ab_2^*_{\cdot_{tm}} \qquad \text{C.}$$

The procedures and their application are all familiar to those skilled in the art and accordingly may be utilized within the scope of the present invention. The "competitive" procedure, Procedure A, is described in U.S. Pat. Nos. 3,654,090 and 3,850,752. Procedure C, the "sandwich" procedure, is described in U.S. Pat. Nos. RE 31,006 and 4,016,043. Still other procedures are known such as the "double antibody," or "DASP" procedure.

In each instance, the NF-κB modulator forms complexes with one or more antibody(ies) or binding partners and one member of the complex is labeled with a detectable label. The fact that a complex has formed and, if desired, the amount thereof, can be determined by known methods applicable to the detection of labels.

It will be seen from the above, that a characteristic property of $Ab_2$ is that it will react with $Ab_1$. This is because $Ab_1$ raised in one mammalian species has been used in another species as an antigen to raise the antibody Ab2. For example, $Ab_2$ may be raised in goats using rabbit antibodies as antigens. $Ab_2$ therefore would be anti-rabbit antibody raised in goats. For purposes of this description and claims, $Ab_1$ will be referred to as a primary or anti-NF-κB modulator antibody, and $Ab_2$ will be referred to as a secondary or anti-$Ab_1$ antibody.

The labels most commonly employed for these studies are radioactive elements, enzymes, chemicals which fluoresce when exposed to ultraviolet light, and others.

A number of fluorescent materials are known and can be utilized as labels. These include, for example, fluorescein, rhodamine, auramine, Texas Red, AMCA blue and Lucifer Yellow. A particular detecting material is anti-rabbit antibody prepared in goats and conjugated with fluorescein through an isothiocyanate.

The NF-κB modulator or its binding partner(s) can also be labeled with a radioactive element or with an enzyme. The radioactive label can be detected by any of the currently available counting procedures. The preferred isotope may be selected from $^3H$, $^{14}C$, $^{32}P$, $^{35}S$, $^{36}Cl$, $^{51}Cr$, $^{57}Co$, $^{58}Co$, $^{59}Fe$, $^{90}Y$, $^{125}I$, $^{131}I$, and $^{186}Re$.

Enzyme labels are likewise useful, and can be detected by any of the presently utilized colorimetric, spectrophotometric, fluorospectrophotometric, amperometric or gasometric techniques. The enzyme is conjugated to the selected particle by reaction with bridging molecules such as carbodiimides, diisocyanates, glutaraldehyde and the like. Many enzymes which can be used in these procedures are known and can be utilized. The preferred are peroxidase, β-glucuronidase, β-D-glucosidase, β-D-galactosidase, urease, glucose oxidase plus peroxidase and alkaline phosphatase. U.S. Pat. Nos. 3,654,090; 203,850, 752; and 4,016,043 are referred to by way of example for their disclosure of alternate labeling material and methods.

In a further embodiment of this invention, commercial test kits suitable for use by a medical specialist may be prepared to determine the presence or absence of predetermined NF-κB modulator activity or predetermined NF-κB modulator activity capability in suspected target cells. In accordance with the testing techniques discussed above, one class of such kits will contain at least the labeled NF-κB modulator or its binding partner, for instance an antibody specific thereto, and directions, of course, depending upon the method selected, e.g., "competitive," "sandwich,"0 "DASP" and the like. The kits may also contain peripheral reagents such as buffers, stabilizers, etc.

Accordingly, a test kit may be prepared for the demonstration of the presence or capability of cells for predetermined NF-κB modulator activity, comprising:

(a) a predetermined amount of at least one labeled immunochemically reactive component obtained by the direct or indirect attachment of the present NF-κB modulator or a specific binding partner thereto, to a detectable label;

(b) other reagents; and (c) directions for use of said kit.

More specifically, the diagnostic test kit may comprise:

(a) a known amount of the NF-κB modulator as described above (or a binding partner) generally bound to a solid phase to form an immunosorbent, or in the alternative, bound to a suitable tag, or plural such end products, etc. (or their binding partners) one of each;

(b) if necessary, other reagents; and (c) directions for use of said test kit.

In a further variation, the test kit may be prepared and used for the purposes stated above, which operates according to a predetermined protocol (e.g. "competitive," "sandwich," "double antibody," etc.), and comprises:

(a) a labeled component which has been obtained by coupling the NF-κB modulator to a detectable label;

(b) one or more additional immunochemical reagents of which at least one reagent is a ligand or an immobilized ligand, which ligand is selected from the group consisting of:

(i) a ligand capable of binding with the labeled component (a);

(ii) a ligand capable of binding with a binding partner of the labeled component (a);

(iii) a ligand capable of binding with at least one of the component(s) to be determined; and (iv) a ligand capable of binding with at least one of the binding partners of at least one of the component(s) to be determined; and (c) directions for the performance of a protocol for the detection and/or determination of one or more components of an immunochemical reaction between the NF-κB modulator and a specific binding partner thereto.

In accordance with the above, an assay system for screening potential drugs effective to modulate the activity of the NF-κB modulator may be prepared. The NF-κB modulator may be introduced into a test system, and the prospective drug may also be introduced into the resulting cell culture, and the culture thereafter examined to observe any changes in the NF-κB modulator activity of the cells, due either to the addition of the prospective drug alone, or due to the effect of added quantities of the known NF-κB modulator.

In accordance with the present invention, a mutant cell line, 5R, was originally isolated as a cellular flat variant of Rat-1 fibroblasts transformed by the Tax protein of human T-cell leukemia virus type 1 (HTLV-1). Tax is known to activate transcription from the HTLV-1 long terminal repeat, to cause permanent activation of many cellular transcription factors including NF-κB and to give rise to cellular transformation (for a review, see Yoshida et al., 1995). 5R cells carry a recessive cellular mutation which abolishes Tax-induced constitutive NF-κB activity, therefore providing a potential mean of identifying a critical molecule involved in Tax-mediated NF-κB activation. Interestingly, 5R cells were found to be resistant to multiple NF-κB activating stimuli besides Tax, suggesting they carried a mutation at a converging regulatory step. 5R cells were used for a genetic complementation approach for the following reasons. First, as the screen was based on the NF-κB-dependent expression of a drug resistance gene, the presence of Tax would ensure restoration of a permanent high NF-κB activity following complementation. Second, Rat-1-derived cells grow well in the presence of a high NF-κB activity. Third, 5R cells are expected to show a transformed phenotype following complementation. Here the genetic complementation of 5R cells is described. By infection with a cDNA expression library cloned into a retroviral vector, complemented clones derived from 5R cells were obtained and expression of the cloned gene, nemo, also complements the defect in the 1.3E2 cell line and show that NEMO is part of the high molecular weight IKK complex and is required for its formation.

Having generally described this invention, a further understanding can be obtained by reference to certain specific examples which are provided herein for purposes of illustration only and are not intended to be limiting unless otherwise specified.

EXAMPLES

Example 1

Materials and Methods

Cells and transfections. The 70Z/3 murine pre-B cell line and the NF-κB unresponsive mutant 1.3E2 were maintained in RPMI medium supplemented with 10% foetal calf serum and 50 $\mu$M β-mercaptoethanol. 70Z/3 and 1.3E2 cells were transiently transfected as described (Courtois et al., 1997). Isolated stable clones were prepared as described (Whiteside et al., 1995). Rat-1 and 5R cells were grown in DMEM supplemented with 10% foetal calf serum and transfected using the calcium phosphate coprecipitation method. For measurement of luciferase activity in transiently transfected Rat-1 or 5R cells, approximately $2\times10^5$ cells were transfected with 0.25 $\mu$g of a reporter plasmid, 0.25 $\mu$g of EF1-lacZ plasmid and 1 $\mu$g of either vector or effector plasmid. Cells were harvested 40 to 45 hours after transfection. The amount of lysate used for luciferase assay was determined on the basis of β galactosidase activity. The results shown are representative of one experiment carried out in duplicate and averaged. Each experiment was repeated at least three times, with similar results.

Phoenix-Eco packaging cells were a kind gift of G. Nolan (Stanford University).

Plasmids. A BLAST search of Genbank with the human IKK-1 cDNA sequence revealed the presence of an EST clones encoding for a single, IKK-1-related cDNA. This clone was obtained from the UK HGMP and the cDNA insert was used to screen an adult human liver cDNA library. Positively hybridizing phage were isolated and both strands of the largest insert obtained were sequenced by the dideoxy termination method (Sequenase, USB). IKK-2 coding sequences was amplified by PCR and inserted into vectors that allowed the in vitro and in vivo expression of proteins fused to the VSV epitope. Rat IKK-1 was amplified by PCR from an EST clone and subcloned into the same vector. The plasmids Igκ-luciferase and SRE-luciferase have been described previously (Courtois et al., 1997); HTLV-1 LTR-luciferase was a kind gift of P. Jalinot (Ecole Normale Suprieure de Lyon).

The plasmid Igκ2bsrH was constructed by ligating a 1.5 kb HindIII/BamHI fragment of the plasmid pSV2bsr (Izumi et al., 1991) with a 5.1 kb HindIII/BamHI fragment of the plasmid cx12lacZ-κB (Fiering et al., 1990) which contains 3 tandem copies of the NF-κB oligonucleotide derived from the IgK sequence (TCAGAGGGGACTTTCCGAG) (SEQ ID NO:3) followed by a minimal IL-2 promoter.

A Tax expression vector, pCntax was constructed by inserting a BamHI fragment of the plasmid pUCwtax (Yamaoka et al., 1996) containing the entire coding sequence of Tax to the unique BamHI site of pCMV-Neo-Bam vector (Baker et al., 1990).

A 2.8 kb PCR product derived from genomic DNA of a blasticidin S-resistant 5R clone was obtained using primers located in the retroviral vector pCTV1 (Whitehead et al., 1995). This PCR product was then digested with SalI, subcloned into pBluescript for sequencing or into the XhoI site of the CMV-hygro vector (a kind gift of F. Aurade, Institut Pasteur).

Reagents. LPS, PMA, poly (I-C), chloroquine and polybrene were from Sigma. Recombinant hIL-1β was from Biogen (Geneva, Switzerland). Recombinant TNF-α was from Genzyme. Blasticidin S was purchased from ICN. Absence of endotoxin contamination in all these reagents, except LPS, was checked with a polymyxin B assay (Shapiro and Dinarello, 1995).

Antisera. Rabbit antiserum against IκBα was a kind gift of J. DiDonato and M. Karin (UCSD). Anti-VSV was mouse monoclonal P5D4. Anti-Tax was mouse monoclonal MI73 (Mori et al., 1987). Anti-IKK-1 antibody was from Santa Cruz. Anti NEMO rabbit polyclonal antiserum (serum 44106) was raised against a TrpE fusion of a fragment encompassing amino acids 30–329 of murine NEMO in the Path11 vector (Spindler et al., 1984).

Preparation of cell extracts. Cells were washed with PBS and resuspended at $10^6$ cells/10 μl in hypotonic solution (10 mM Hepes, pH 7.8, 10 mM KCl, 2 mM MgCl$_2$, 1 mM DTT, 0.1 mM EDTA supplemented with a protease inhibitor cocktail (Boehringer)). After 10 minutes at 4° C., NP40 was added to 1% and the cells centrifuged in a microfuge for 20 seconds. The supernatant, containing the cytoplasmic fraction, was recovered. One volume of 2×Laemmli buffer containing 20% μ-Mercaptoethanol was added and the sample was boiled for 5 minutes. The nuclear pellet was briefly washed with hypotonic buffer and resuspended in 40 μl of extraction buffer (50 mM Hepes, pH 7.8, 50 mM KCl, 350 mM NaCl, 0.1 mM EDTA, 1 mM DTT, 0.1 mM PMSF, 10% glycerol). After a 30 minutes incubation on ice, with occasional agitation, the DNA was pelleted by centrifuging at 14000 rpm for 10 minutes. The supernatant, containing the nuclear fraction, was recovered and quickly frozen on dry ice. Samples were stored at −80° C.

Preparation of S100 extracts and gel filtration analysis. Fifty millions cells were washed in PBS and resuspended in 500 μl of 50 mM Tris pH 7.5, 1 mM EGTA. Cells were lysed by thirty passages through a 26-gauge needle. After centrifugation for 10 minutes at 15000 rpm the supernatant was recovered and complemented with 1 mM DTT, 0.025% Brij and a cocktail of proteases and phosphatases inhibitors. S100 were prepared by centrifuging the cytoplasmic extracts for 30 minutes at 52000 rpm in a TLA 100.2 rotor (Beckman). After adding 10% glycerol, the S100 extracts were quickly frozen in dry ice and stored in liquid nitrogen. Gel filtration chromatography was carried out on a Superose 6 column (Pharmacia) precalibrated with Aldolase (158 kD), Catalase (232 kD), Ferritin (440 kD) and Thyroglobulin (669 kD). Five hundred μl fractions were recovered and directly analyzed by Western blotting or immunoprecipitated with anti-NEMO. Silver staining of the fractions was performed with a Silver Stain Plus Kit (Biorad).

Western blot analysis. Proteins from cytoplasmic extracts were fractionated on 10% SDS-polyacrylamide gels, transferred onto Immobilon membranes (Millipore), and blots were revealed with an enhanced chemiluminescence detection system (ECL, Amersharn).

In vitro translation and crosslinking. Translations and co-immunoprecipitation experiments were performed as described previously using TNT kits (Promega) (Kieran et al., 1990). For dimerization experiments, translation reactions were diluted thirty times with phosphate buffered saline, treated with glutaraldehyde at room temperature for 20 minutes, with 100 mM of Tris-HCl (pH 7.4) for 20 minutes and subjected to immunoprecipitation after addition of an equal volume of TNT buffer (NaCl 200 mM, Tris-HCl 20 mM pH 7.5, Triton X-100 1% supplemented with protease and phosphatase inhibitors).

Immunoprecipitations and kinase assays. Cytoplasmic extracts were subjected to immunoprecipitation with anti-IKK-1 antibody, anti-NEMO or pre-immune serum in TNT buffer and collected on protein A-Sepharose beads, which were then washed 3 times with TNT buffer and three times with kinase buffer (20 mM Hepes, 10 mM MgCl$_2$, 100 μM Na$_3$VO$_4$, 20 mM β-glycerophosphate, 2 mM DTT, 50 mM NaCl, pH 7.5). Kinase reactions were for 30 minutes at 30° C. using 5 μCi of [γ-$^{32}$P]-ATP and GST-IκBα (1–72) wild type or GST-IκBα (1–72) S32A/S36A mutant protein as substrates. The reaction products were analyzed on 10% SDS-polyacrylamide gels and revealed by autoradiography for three hours at room temperature.

Electrophoretic mobility shift assays. Five μg of nuclear extracts were added to 15 μl of binding buffer (10 mM Hepes pH 7.8, 100 mM NaCl, 1 mM EDTA, 10 % glycerol final), 1 μg poly (dI-dC) and 0.5 ng $^{32}$P-1-labeled κB probe derived from the H-2K$^b$ promoter (Kieran et al., 1990), and incubated for 30 minutes at room temperature. Samples were run on a 5% polyacrylamide gel in 0.5×TBE.

Viral stocks and infection. T28 cells, a murine T cell hybridoma (Pyszniak et al., 1994) were cultured in Dulbecco's modified Eagle's medium supplemented with 10% fetal bovine serum. Total mRNA from exponentially growing T28 cells was used as template for cDNA synthesis, using random hexamer primers. Procedures for cDNA synthesis and cloning were as described previously (Whitehead et al., 1995). The cDNA was ligated into pCTV1 (Whitehead et al., 1995), yielding 3.5×10$^6$ cDNA clones. Complexities of the libraries were as follows: L35: 470,000 clones (3.5 kb & up); L36: 600,000 clones (2.2–3.5 kb). The Phoenix-Eco packaging cell line was used for transient transfection with DNA from the L35 or L36 libraries. To determine the virus titer on 5R cells, a cDNA library (L20) cloned into the pCTV3 vector (Whitehead et al., 1995) which carries a hygromycin resistance gene was transfected by the calcium phosphate method into Phoenix-Eco cells and the resultant supernatants were titered by the appearance of hygromycin resistant 5R cells. This library produced viral titers of 2–3×10$^5$/ml. We produced viral supernatants for complementation experiments by transfecting approximately 1.5×10$^7$ Phoenix cells plated 24 hours before with 20 μg of the L35 or L36 library DNA in the presence of 25 μM chloroquine. Supernatants were recovered every 12 hours from 36 to 72 hours after transfection and either immediately used for infection of h12 cells or snap frozen in dry ice and stored at −80° C. Approximately 10$^6$ h12 cells were plated 12 to 15 hours before infection on a 100 mm petri dish and exposed to 3 ml of viral supernatant in the presence of 3 ml of conditioned medium and 10 μg/ml of polybrene. Twelve hours after starting the infection, the viral supernatant was removed and cells were cultured for an additional 24 hours in normal growth medium. Blasticidin S was added to a final concentration of 10 μg/ml 36 hours after infection. The selection medium was replaced at least every 5 days and the resultant cell clones were isolated with cloning cylinders. We used a total of 30×10$^6$ h12 cells for infection with virus stock obtained using 20 μg of L35 or L36 library DNA and finally isolated similar number of independent cell clones for the two cDNA libraries.

Results

Characterization of the Mutant Cell Line 5R

Figure 1B:
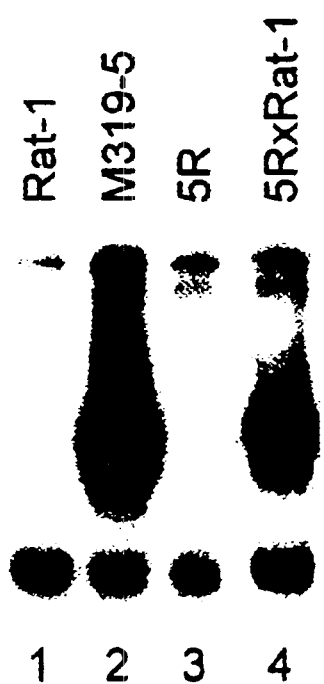
Figure 1E:
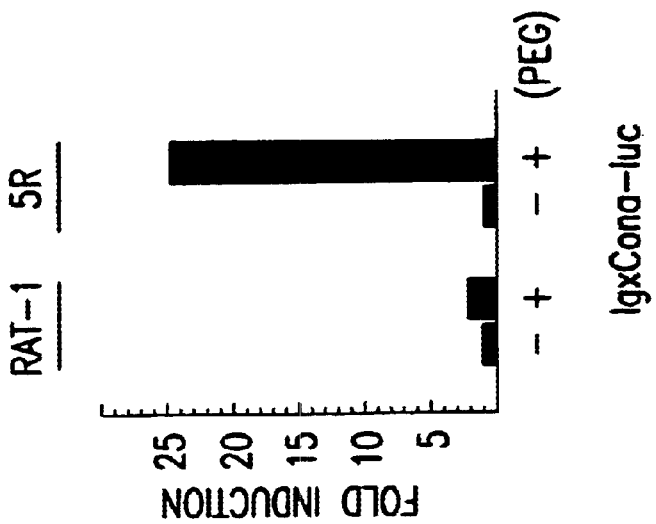
Figure 1D:
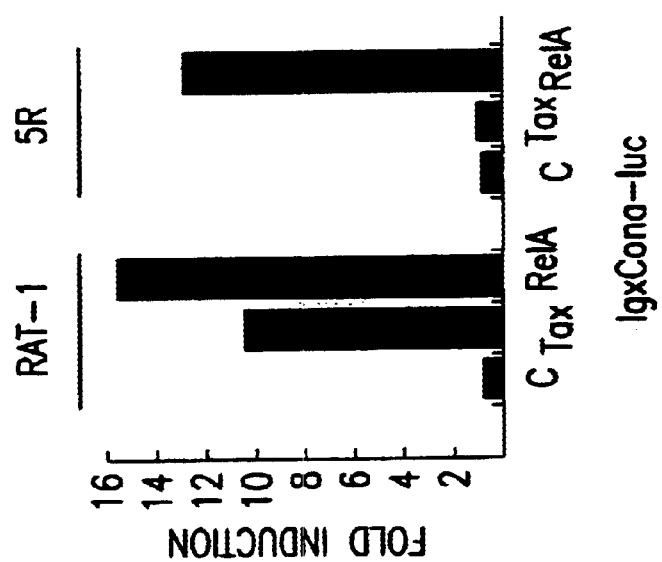
Figure 1C:
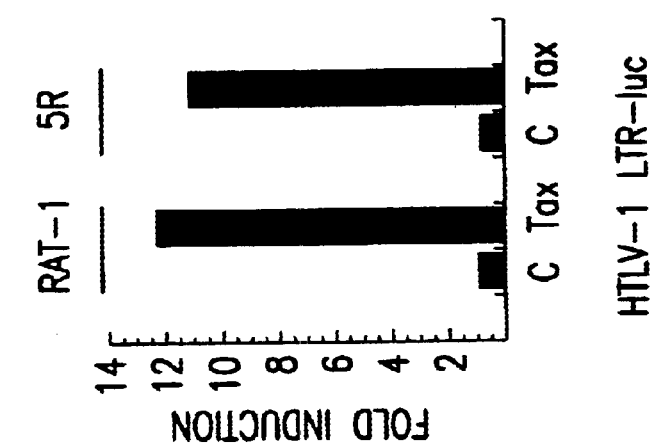

Spontaneous flat revertant cells were isolated from M319-5 cells, a clone of Rat-1 fibroblasts transformed by a mutant Tax protein competent to activate NF-1-κB, but unable to stimulate HTLV-1 long terminal repeat (LTR)-directed transcription (Yamaoka et al., 1996). All of them except one (clone 5R) had lost Tax expression. 5R cells express Tax at a level comparable with the parental cells (FIG. 1A, lane 3), but are defective in Tax-1 induced NF-κB DNA-binding activity (FIG. 1B, lane 3). Stable expression of wild-type Tax failed to re-transform 5R cells, while forced expression of constitutively active c-Ha-Ras or v-Src protein transformed 5R cells as efficiently as the parental Rat-1 cells. Transient expression of wild-type Tax fully activated HTLV-I LTR-directed, but not NF-κB dependent transcription in 5R cells (FIGS. 1C, D). On the other hand, transient expression of RelA or activated c-Ha-Ras strongly stimulated NF-κB- or Serum Responsive Element-dependent transcription respectively, in 5R as well as in Rat-1 cells (FIG. 1D and data not shown). These results suggest that 5R cells carry a mutation(s) which abrogates Tax-mediated NF-κB activation.

The phenotype of the mutation was next analyzed by somatic cell hybridization. Since 5R cells express Tax, they are expected to restore Tax-induced NF-κB activity after hybridization with parental cells if the mutation is recessive. Hybridization of 5R cells with Rat-1 cells carrying an integrated NF-κB-dependent reporter gene induced a strong transcriptional activity when compared with the control hybridization (FIG. 1E). We also established a pooled population of stable hybrids between 5R and Rat-1 cells and found that they exhibited a transformed phenotype (data not shown) and contained high NF-κB DNA-binding activity (FIG. 1B, lane 4). These results indicate that the phenotype of the mutation in 5R cells is recessive and therefore should be amenable to genetic complementation.

Figure 2A:
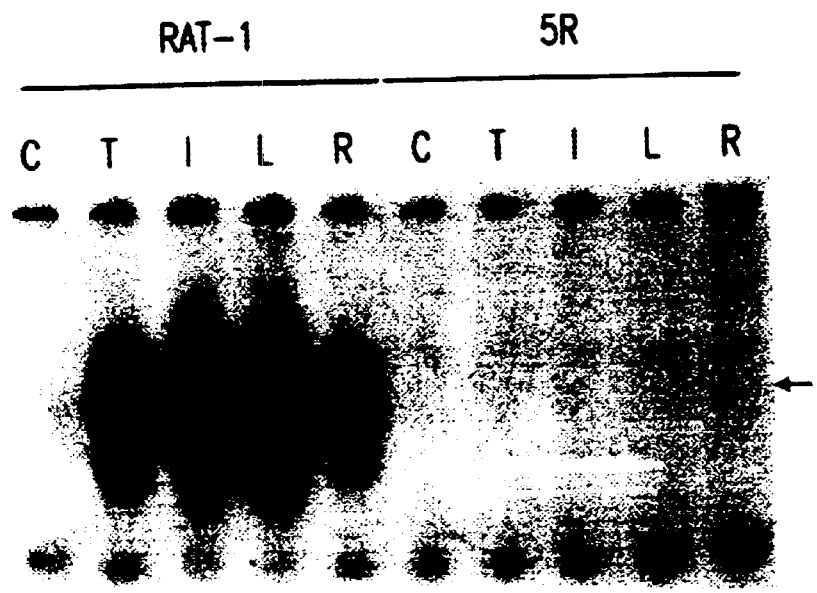
Figure 2B:
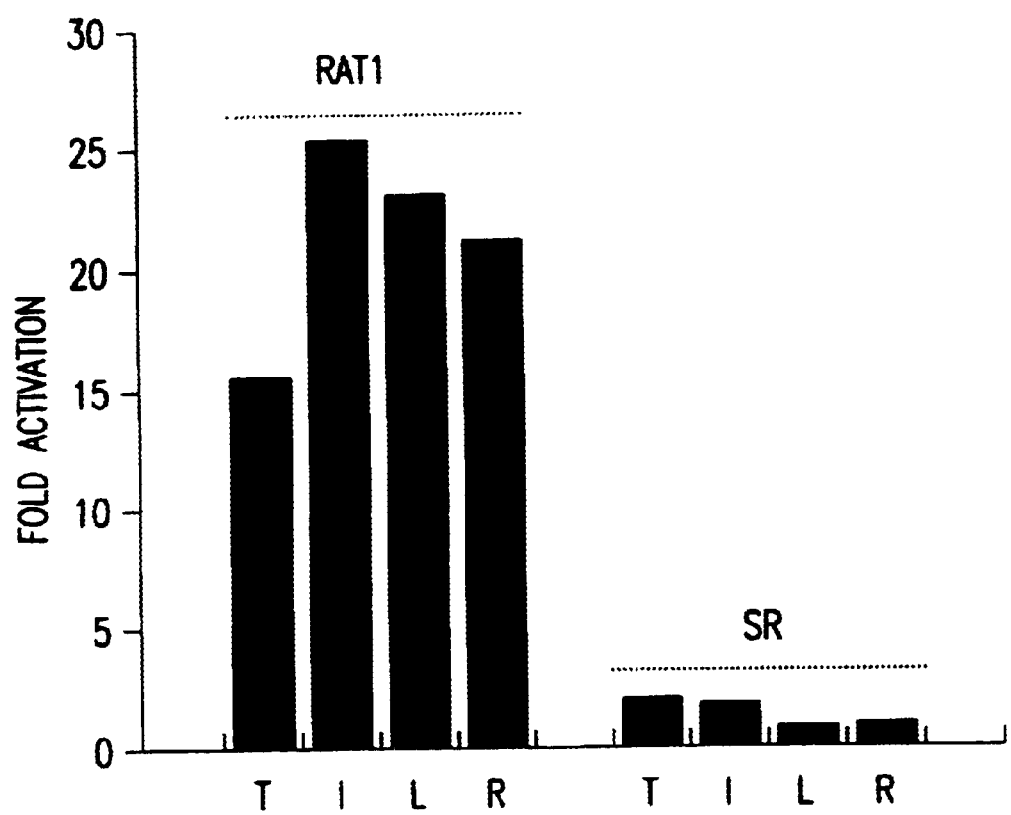
Figure 2C:
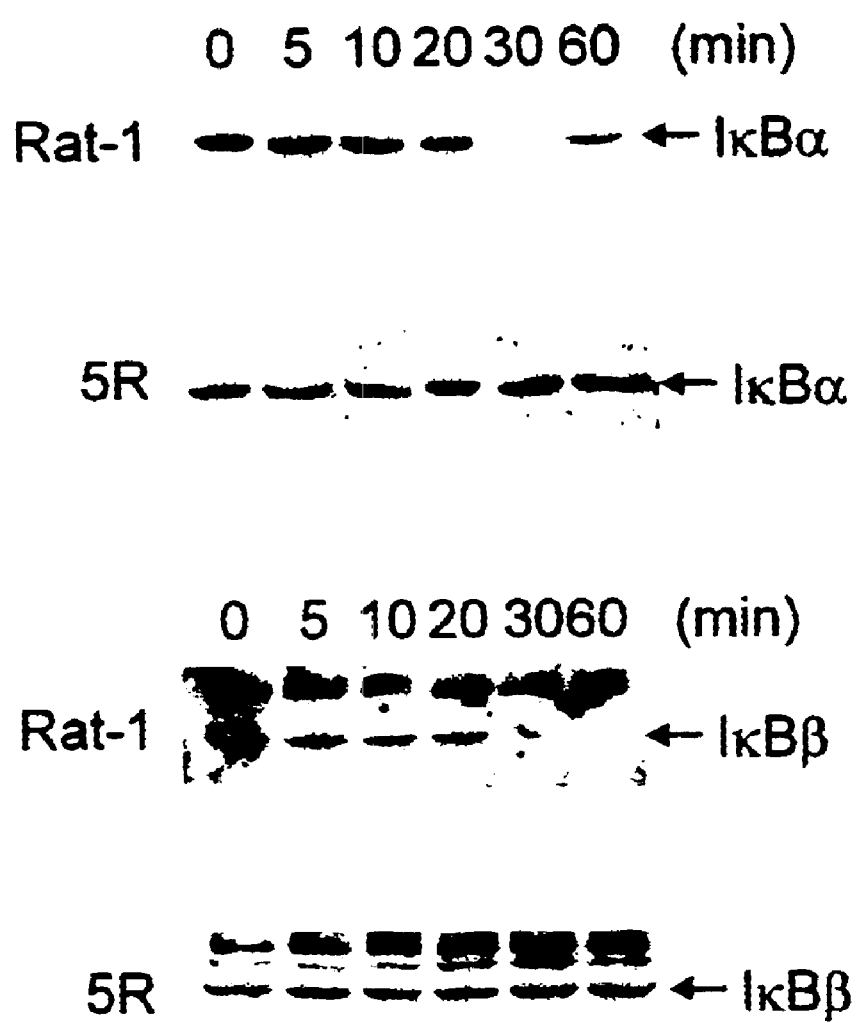

Rat-1 cells normally activate NF-κB in response to diverse external stimuli, including tumor necrosis factor-α (TNF-α), interleukin-1 (IL-1), lipopolysaccharide (LPS) or double stranded RNA (dsRNA). Interestingly, none of these stimuli was able to induce NF-κB DNA-binding activity in 5R cells (FIG. 2A). This result was further confirmed by transient transfection with an NF-κB-dependent reporter gene (FIG. 2B). In order to identify the step at which NF-κB signaling is affected, the levels of IκB proteins were examined in cells stimulated with LPS. As shown in FIG. 2C, LPS stimulation led to a complete loss of IκBα and of IκBβ in Rat-1 cells followed by re-appearance of IκBα 60 minutes after stimulation. In contrast, the levels of the two IκB proteins in 5R cells were virtually unaffected by LPS treatment. Taken together, one can conclude that 5R cells carry a recessive mutation(s) at a converging regulatory step leading to inducible degradation of IκB proteins. Finally, the possibility that 5R cells might be defective in one of the functional IκB kinases was addressed. Stable transfection of 5R cells with plasmids encoding either IKK-1 or IKK-2 did not restore NF-κB activity.

Molecular Cloning of NEMO

For complementation experiments, a selection system was established by preparing sublines of 5R cells capable of expressing an NF-κB-dependent inducible drug resistance gene. A conditional drug resistance gene, pIgKlbs$\mu$H contains both a hygromycin resistance gene under the control of the HSV1 thymidine kinase gene promoter, and the blasticidin deaminase gene (Izumi et al., 1991) linked to a minimal IL-2 promoter following three repeats of the immunoglobulin κ light chain NF-κB binding site. Stable transfection of the parental Tax transformed cells with this construct using hygromycin selection followed by selection with blasticidin S resulted in numerous surviving colonies, whereas none could be observed for 5R cells. Hygromycin-resistant 5R clones were tested for survival in the presence of blasticidin S following simple co-culture or hybridization with normal Rat-1 cells. One of the 5R clones, h12, was chosen at random for further experiments as being able to survive a high dose of blasticidin S selection after the hybridization, but showing absolutely no survival at a low concentration of the drug without the hybridization step. A high NF-κB DNA-binding activity was detected in stable h12/Rat-1 hybrids, a result of activation by Tax following complementation of the defect of h12 cells.

Figure 4A:
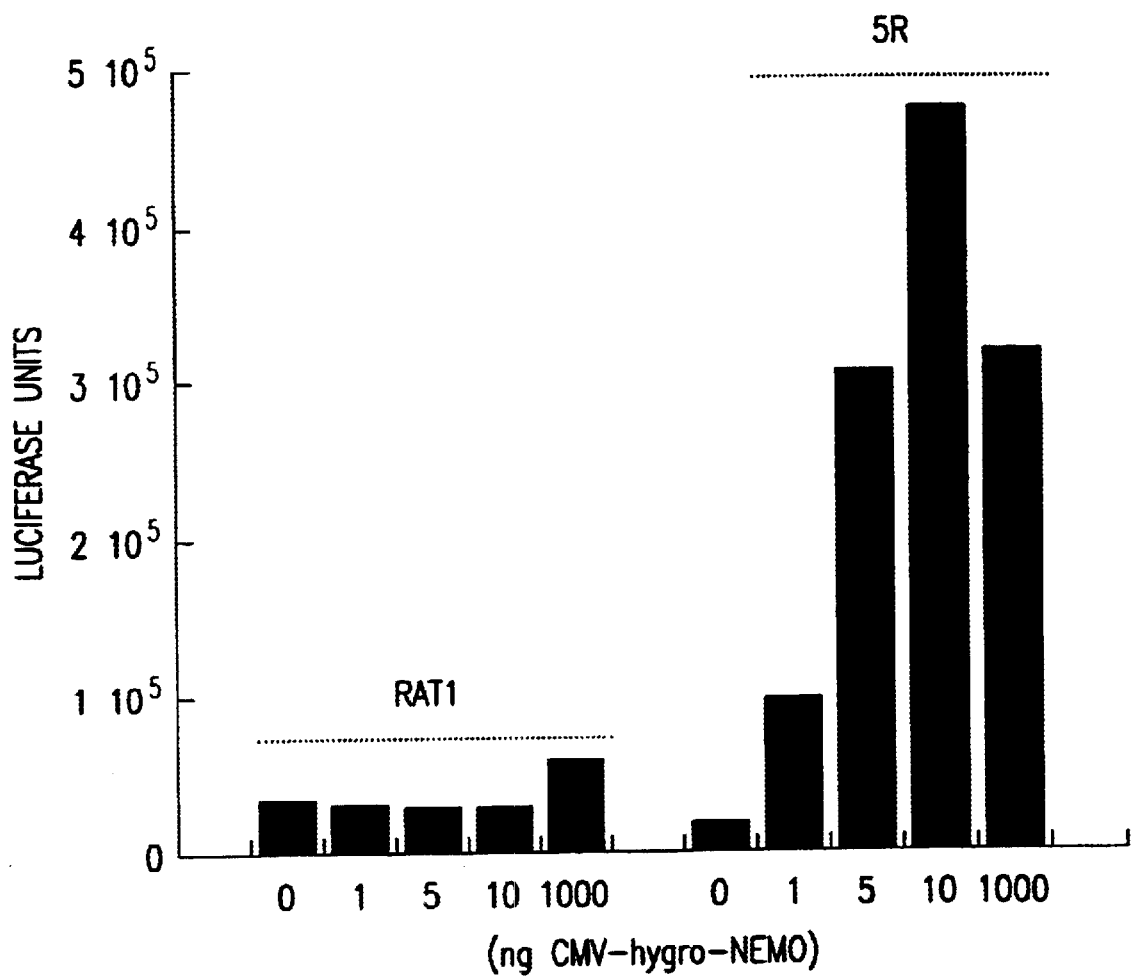
Figure 4B:
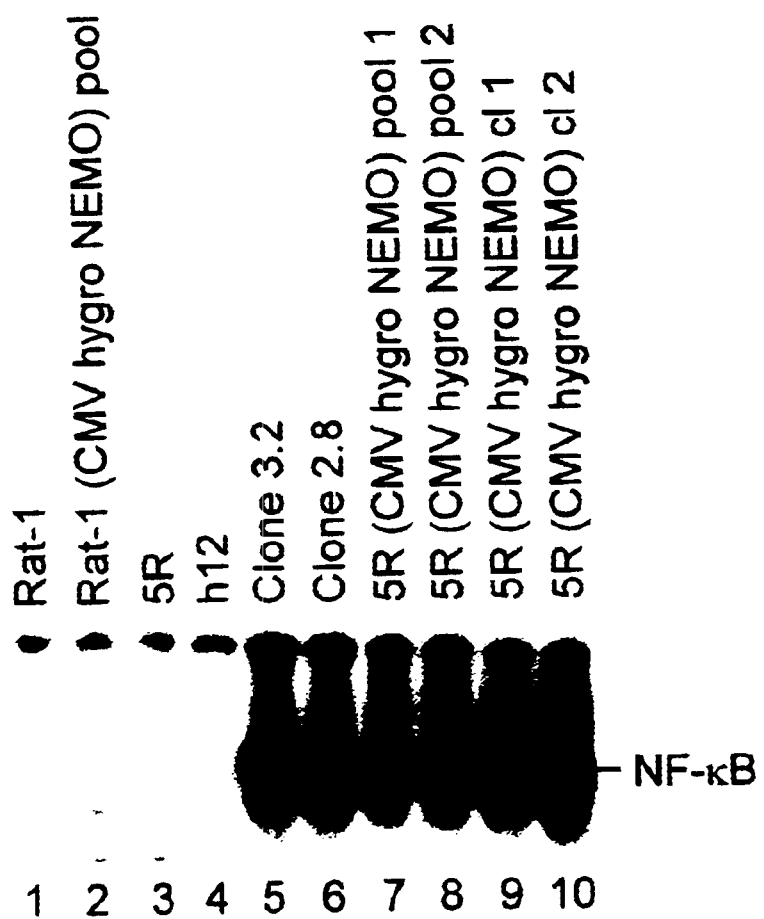
Figure 4C:
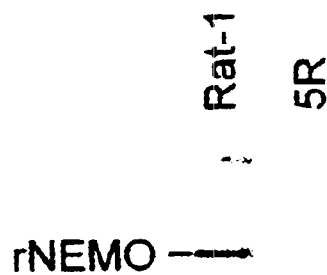

Approximately $30 \times 10^6$ h12 cells were infected with retroviruses carrying a cDNA expression library derived from the T28 murine T cell hybridoma cell line (Whitehead et al., 1995). Viral supernatants were produced by transient transfection of Phoenix cells with the retroviral constructs giving titers in the range of $2 \times 10^5 - 3 \times 10^5$/ml. Selection with blasticidin S was started 36 hours after viral infection. In 20 to 30 days, a total of more than 40 independent clones were obtained and 20 were tested for their NF-κB DNA-binding activity. All clones except one contained high levels of DNA-binding activity and clearly showed a transformed phenotype (FIG. 4B, lanes 5–6). Polymerase chain reaction-mediated amplification of genomic DNAs from seven clones resulted in a provirus-derived specific band with a size of 3.2 kb, while 33 other clones carried a 2.8 kb insert. Southern blot analysis of the 3.2 kb insert showed cross hybridization with the 2.8 kb fragment. Sequencing analysis of the amplified 2.8 kb cDNA showed that it contained an open reading frame predicted to encode a previously unknown 48 kDa polypeptide, which we have named NEMO (NF-κB Essential MOdulator) (FIG. 3). This molecule is acidic (pI 5.66) and unusually rich in glutamic acid and glutamine (13 % each). In addition, it contains a putative leucine zipper motif (amino acids 315 to 342). To characterize its function, Rat-1 or 5R cells were transfected with a mammalian expression vector capable of expressing NEMO. Cotransfection of SR cells with a very small amount of NEMO and an NF-κB-dependent reporter gene resulted in a strong reporter gene activation by endogenous Tax, whereas its overexpression in Rat-1 cells barely activated the reporter construct (FIG. 4A). Rat-1 or 5R cells stably expressing NEMO were then established. As expected, stable expression of NEMO (under the control of the strong CMV promoter) in wild-type Rat-1 cells did not give rise to detectable NF-κB activity (FIG. 4B, lane 2). On the other hand, two pooled populations derived from NEMO-transformed 5R cells and two isolated clones showed high levels of NF-κB DNA-binding activity (lanes 7–10), indicating that stable NEMO expression can complement the defect in 5R cells.

A polyclonal antibody was raised against the region encompassing amino acids 60–329 of NEMO and used to analyze its expression in 5R cells. Whereas the protein could be readily detected as a single 48 kD band in Rat1 cytoplasmic extracts (FIG. 4C), no NEMO band could be observed in 5R cells. In addition, no truncated form of the protein could be 10 detected. Thus, the defective phenotype of 5R cells results from the absence of the NEMO to protein.

Complementation of the 1.3E2 Mutant Cell Line by NEMO

The characterization of another mutant cell line, the 70Z/3-derived mutant 1.3E2, was recently reported that exhibits a defect in NF-κB activation (Courtois et al., 1997). In this cell line NF-κB is not activated in response to a large set of stimuli, among them LPS, IL-1, PMA, dsRNA or TNF. This is due to a lack of IκBα, IκBβ and IκBε degradation. Since phosphorylation of IκBα on Ser 32 and 36 is not observed after stimulation, a converging step preceding the IκB phosphorylation step or the phosphorylation step itself was proposed to be deficient in 1.3E2.

Figure 5A:
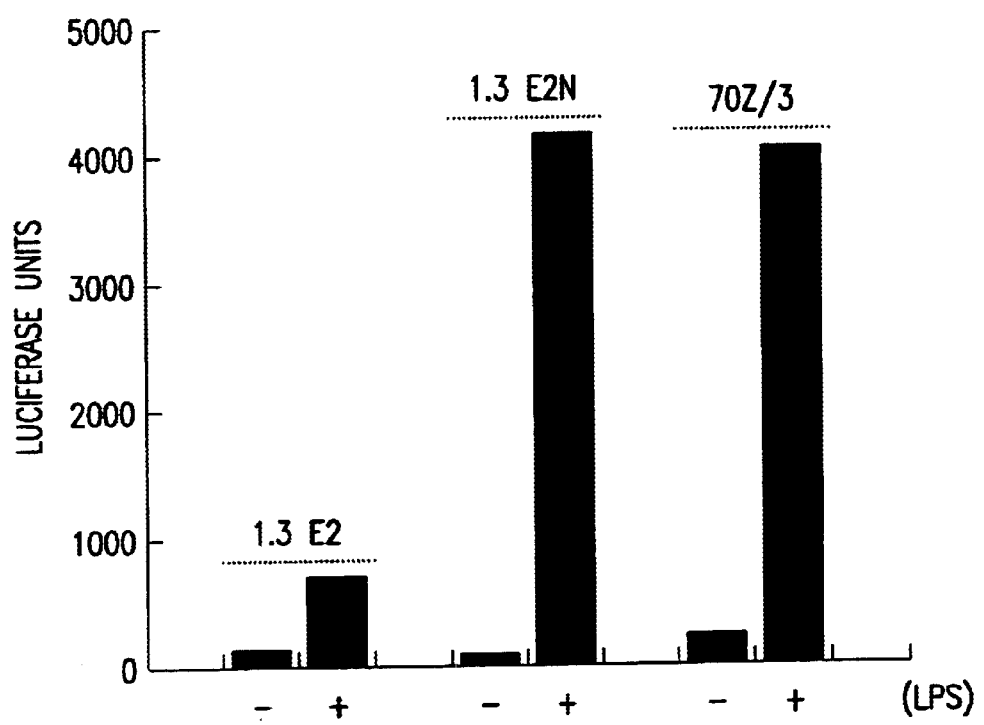

Since the 1.3E2 phenotype shares many similarities with the 5R phenotype, it was tested whether NEMO could complement 1.3E2. Strikingly, as shown in FIG. 5A, transient transfection of 1.3E2 with a vector expressing NEMO allowed the recovery of a wild-type NF-κB activation level after LPS stimulation. Such an effect was clearly stimulus-specific, indicating that NEMO overexpression by itself was unable to activate NF-κB. Complemention was also observed in the case of two other stimuli, IL-1 and PMA, although with less efficiency in the latter case.

Figures 5B, 5C:
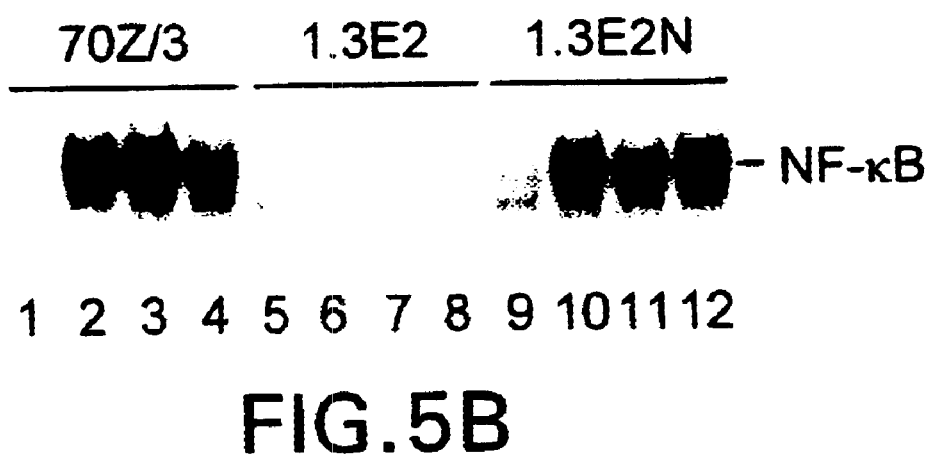

1.3E2 cells stably expressing NEMO (1.3E2N) were also prepared and tested for complementation. A mobility shift experiment presented in FIG. 5B confirmed the results of the transient transfection experiments described above. NF-κB activation in response to LPS, IL-1 or PMA was found to be similar in wild-type 70Z/3 and 1.3E2N. Moreover, an immunoblot analysis revealed that NEMO is undetectable in 1.3E2 cells (FIG. 5C). These results demonstrate that, as for 5R cells, the phenotype of the 1.3E2 mutant cell line is due to the absence of NEMO.

NEMO is Part of the IκB Kinase Complex

Since NEMO appears to be critically involved in NF-κB activation by a large set of stimuli and complements cells defective in IκB phosphorylation, an attractive possibility would be that it constitutes a subunit of the 600–800 kD kinase complex that phosphorylates IκB. Therefore, it was investigated whether NEMO is associated with the inducible IκB kinase activity (FIG. 6). To demonstrate this point immune complex kinase assays were conducted on Rat-1 or 5R cells. The antiserum against NEMO immunoprecipitated a specific endogenous IκBα kinase activity from wild type cells stimulated with TNF-α. Absense of kinase activity in NEMO-1 immunoprecipitates from 5R cells and lack of phosphorylation of a mutant IκBα polypeptide (S32A, S36A) established the specificity of the antiserum and kinase activity, respectively. Thus, NEMO is associated with an inducible endogenous IκBα kinase activity. As reported previously, an anti-IKK-1 antibody brought down a specific IκBα kinase activity from wild type cells stimulated with TNF-α for 5 minutes. Interestingly, no inducible IκBα kinase activity was observed in IKK-1 precipitates from 5R cell extracts.

Figure 7A:
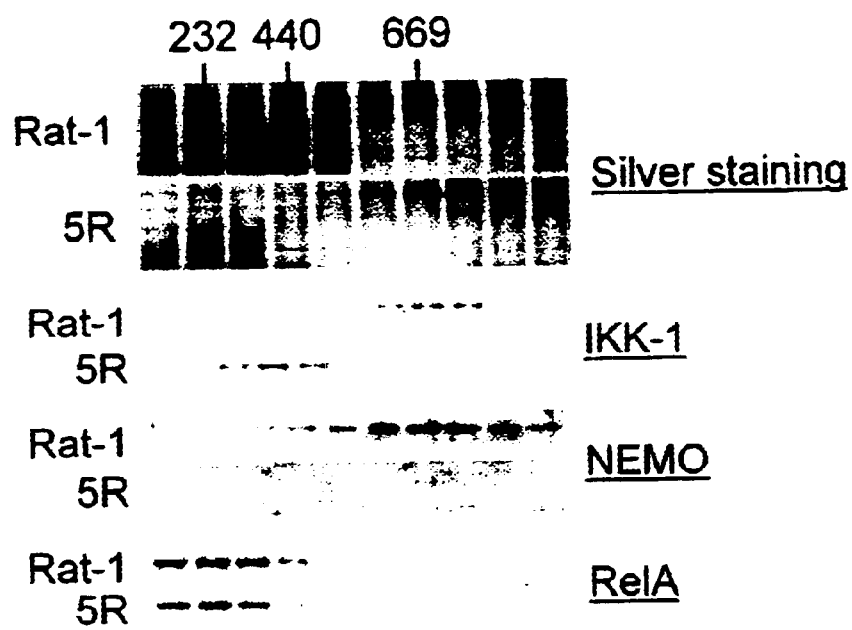
Figure 7B:
Figure 7C:

In order to confirm that NEMO is an integral part of the IκB kinase complex, and to determine whether it is stably associated with it before stimulation, S100 extracts were prepared from Rat-1 cells and fractionated on a Superose 6 gel filtration column. Elution of the IκB kinase, monitored with an anti-IKK-1 antibody, was mostly observed in fractions containing proteins of 600 to 800 kD, as previously reported (FIG. 7A). When NEMO elution was examined, an identical profile was obtained. Immunoprecitation of the NEMO-containing fractions with an anti-NEMO antibody allowed us to co-1 immunoprecipitate IKK-1 (FIG. 7B). NEMO is therefore a stable component of the 600–800 kDa IκB kinase complex.

Quite remarkably, when 5R extracts were analyzed with the IκK-1 antibody, the elution peak appeared shifted toward fractions containing proteins of 300–450 kD instead of 600–800 kD (FIG. 7A). Since the overall elution profile, as checked either by silver staining (FIG. 7A, top panel) or by Western blotting against RelA (FIG. 7A, bottom panel) or p105 (data not shown), was identical between Rat-1 and 5R, this observation demonstrated the requirement of NEMO for building a high molecular weight IκB kinase complex. Moreover, the absence of IκB kinase activity in 5R cells after stimulation (see above) indicates that the lower molecular weight kinase complex is refractory to activation.

NEMO Can Form Homodimers and Interacts Directly With IκK-2

The presence of a leucine zipper-1 like motif in NEMO led us to ask whether this molecule could dimerize. Glutaraldehyde crosslinking experiments (FIG. 7C) demonstrated that NEMO was indeed able to form homodimers.

Figure 7D:
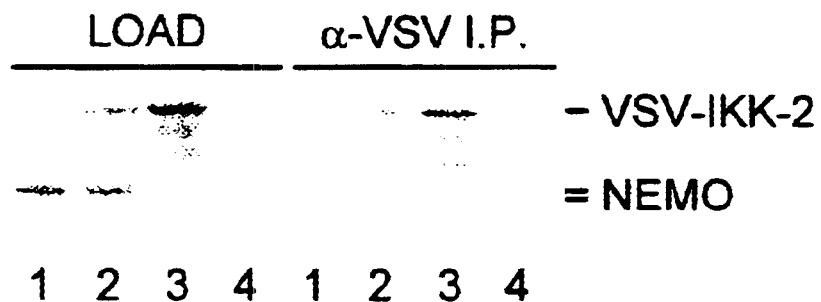

Since NEMO is part of the IκB kinase complex, direct interactions with known components of the complex were examined, namely the two catalytic subunits IKK-1 and IKK-2. An in vitro analysis was conducted using $^{35}$S-1-labeled proteins translated in wheat germ extracts (WGE). After co-translation of VSV-IKK-2 and NEMO, followed by anti-VSV imunoprecipitation, NEMO was readily detected in the immunoprecipitate (FIG. 7D). The converse experiment, using NEMO plus VSV-IKK-2 and imunoprecipitating with anti-NEMO allowed the detection of VSV-IKK-2 in the immunoprecipitate. Interestingly, such an interaction could barely be observed with IKK-1, suggesting a potential functional divergence between the two IKKs.

One approach aimed at identifying components of the NF-κB signaling pathway which has not been widely used so far is to generate mutant cell lines which are unresponsive to one or several NF-κB activating signals, and to try and complement these cell lines with genomic or cDNA libraries (Ting et al., 1996). Here is used a spontaneous mutant (called 5R) of a HTLV-1 transformed Rat-1 fibroblastic cell line, which had lost its transformed morphology. This mutation was accompanied by disappearance of Tax-induced NF-κB activity, as measured by bandshift and transactivation assays. In addition, LPS-, IL-1-dsRNA- or TNF-1-induced NF-κB DNA-binding activity could not be observed in the 5R cell line. However other signaling pathways seemed to be still functional. Importantly, cell fusion experiments demonstrated that the mutation was recessive. All these observations prompted an attempt to complement this cell line. The selection was based on introduction into these cells, prior to complementation, of a gene encoding resistance to the antibiotic blasticidin S driven by multimerized NF-κB binding sites. Only the complemented cells would be expected to become resistant to blasticidin S treatment, a result of transactivation of the blasticidin S resistance gene by endogenous Tax. More than forty independent blasticidin S-resistant clones were isolated, and bandshift analysis demonstrated the presence of a p50/relA complex in 19 analyzed clones out of 20, with an intensity similar to that observed following stimulation of wild-type Rat-1 cells with LPS or TNF. PCR amplification of DNA from 40 independent clones using primers localized in the flanking regions of the retroviral vector yielded two cross-hybridizing fragments, of 2.8 and 3.2 kb. Sequencing of the amplified cDNA revealed that the 2.8 kb insert contains an open reading frame encoding a previously undescribed 412 amino acid protein, that we called NEMO. This protein is acidic (PI 5.66), unusually rich in glutamic acid and glutamine (13% each) and also contains a putative leucine zipper motif (amino acids 315 to 342).

Transfection of NEMO complemented the mutation in 5R cells. This led to the conclusion that NEMO is necessary for activation of NF-κB by Tax. However the presence of endogenous Tax in the 5R cell line precluded the analysis of NEMO involvement in other NF-κB activation pathways. This problem was circumvented by the use of 1.3E2, another mutant cell line that we previously characterized (Courtois et al., 1997). NF-κB activation, degradation of the three known IκB inhibitors, as well as induced phosphorylation of IκBA could not be observed following PMA, LPS, IL-1 or dsRNA treatment of this cell line. NEMO cDNA was stably introduced into 1.3E2 and it was observed that NF-κB activation by at least three of these stimuli (LPS, PMA and IL-1) was restored. Therefore the NEMO protein is involved in the response to at least four NF-κB activating stimuli.

An interesting conclusion one can draw from complementation of the 5R cells, which regain a transformed phenotype when stably transfected with NEMO, is that NF-κB activity seems to be required for cell transformation by Tax (at least in this cell system). There have been conflicting data in the literature concerning the actual involvement of NF-κB in Tax-induced transformation (Kitajima et al., 1992; Smith and Greene, 1991; Yamaoka et al., 1996).

The next question concerned the actual function of NEMO. Since this molecule appears to be involved in all tested NF-κB activating pathways, an obvious possibility was that it constituted one subunit of the high molecular weight IκB kinase complex. Three arguments are in favor of this hypothesis: First, immunoprecipitation of NEMO from Rat-1 cells pulled down a bonafide IκBα kinase activity, specific for the 2 N-terminal serines. Second, NEMO elutes as a 600–800 kDa peak from a gel filtration column performed on extracts from unstimulated Rat-1 cells, as does IκK-1. Third, immunoprecipitation of NEMO from Rat-1 fractions ranging from 600 to 800 KDa brings down IκK-1.

The possible interaction of NEMO with the 2 catalytic subunits of the complex was tested, IKK-1 and IKK-2. In vitro cotranslation of IKK-2 and NEMO in wheat germ extract followed by immunoprecipitation demonstrated that the two proteins could interact with each it other. In contrast an interaction between NEMO and IKK-1 could barely be detected under these conditions. NEMO can also form homodimers.

IKK-1 can be detected in a 300–450 kD complex in 5R cells, therefore indicating that NEMO is required for the formation of a 600–800 kDa functional IKK complex, and probably plays a role as a structural component of this complex.

It was unexpected that two independently isolated mutant cell lines could be complemented by the same cDNA. The selection for LPS-unresponsive derivatives of 70Z/3 yielded several types of mutant cell lines, but only 1.3E2 was also unresponsive to other NF-κB activating stimuli, and the fact that it grows faster than the wild-type 70Z/3 probably facilitated its isolation. In Tax transformed Rat-1 cells, 5R was the only NF-κB defective cellular revertant which could be isolated. Mutating the nemo gene might be the only means of knocking out NF-κB activation by a single gene mutation.

The following references are cited herein, and should be considered to be incorporated herein by reference in their entireties:

References

Baker, S. J., Markowitz, S., Fearon, E. R., Willson, J. K., and Vogelstein, B. (1990). Science 249, 912–915.
Baldwin, A. S. (1996). Annu Rev Immunol 14, 649–683.
Chen, Z. J., Parent, L., and Maniatis, T. (1996). Cell 84, 853–862. Courtois, G., Whiteside, S. T., Sibley, C. H., and Israel, A. (1997). Mol Cell Biol 17, 1441–1449.
Darnell, J. E., Jr., Kerr, I. M., and Stark, G. R. (1994). Science 264, 1415–1421.
Didonato, J. A., Hayakawa, M., Rothwarf, D. M., Zandi, E., and Karin, M. (1997). Nature 388, 548–554.
Fiering, S., Northrop, J. P., Nolan, G. P., Mattila, P. S., Crabtree, G. R., and Herzenberg, L. A. (1990). Genes Dev 4, 1823–1834.
Izumi, M., Miyazawa, H., Kamakura, T., Yamaguchi, I., Endo, T., and Hanaoka, F. (1991). Exp Cell Res 197, 229–233.
Kieran, M., Blank, V., Logeat, F., Vandekerckhove, J., Lottspeich, F., LeBail, O., Urban, M. B., Kourilsky, P., Baeuerle, P. A., and Israel, A. (1990). Cell 62, 1007–1018.
Kitajima, I., Shinohara, T., Bilakovics, J., Brown, D. A., Xu, X., and Nerenberg, M. (1992). Science 258, 1792–1795.
Lee, F. S., Hagler, J., Chen, Z. J., and Maniatis, T. (1997). Cell 88, 213–222.
May, M. J., and Ghosh, S. (1998). Immunology Today 19, 80–88.
Mercurio, F., Zhu, H. Y., Murray, B. W., Shevchenko, A., Bennett, B. L., Li, J. W., Young, D. B., Barbosa, M., and Mann, M. (1997). Science 278, 860–866.
Mori, K., Sabe, H., Siomi, H., Iino, T., Tanaka, A., Takeuchi, K., Hirayoshi, K., and Hatanaka, M. (1987) J Gen Virol 68, 499–50.
Pyszniak, A. M., Welder, C. A., and Takei, F. (1994). J Immunol 152, 5241–5249.
Regnier, C. H., Song, H. Y., Gao, X., Goeddel, D. V., Cao, Z., and Rothe, M. (1997). Cell 90, 373–383.
Shapiro, L., and Dinarello, C. A. (1995). Proc Natl Acad Sci USA 92, 12230–12234.
Smith, M. R., and Greene, W. C. (1991). J Clin Invest 88, 1038–1042.
Spindler, K. R., Rosser, D. S., and Berk, A. J. (1984). J Virol 49, 132–141.
Ting, A. T., Pimentel-Muinos, F. X., and Seed, B. (1996). EMBO J 15, 6189–6196.
Velazquez, L., Fellous, M., Stark, G. R., and Pellegrini, S. (1992). Cell 70, 313–322.
Verma, I. M., Stevenson, J. K., Schwarz,.E. M., Van Antwerp, D., and Miyamoto, S. (1995). Genes Dev 9, 2723–2735.
Whitehead, I., Kirk, H., and Kay, R. (1995) Mol Cell Biol 15, 704–710.
Whiteside, S. T., Ernst, M. K., LeBail, O., Laurent-Winter, C., Rice, N. R., and Israel, A. (1995). Mol Cell Biol 15, 5339–5345.
Woronicz, J. D., Gao, X., Cao, Z., Rothe, M., and Goeddel, D. V. (1997). Science 278, 866–869.
Yamaoka, S., Inoue, H., Sakurai, M., Sugiyama, T., Hazama, M., Yamada, T., and Hatanaka, M. (1996). EMBO J 15, 873–887.
Yoshida, M., Suzuki, T., Fujisawa, J., and Hirai, H. (1995). Curr Top Microbiol Immunol 193, 79–89.
Zandi, E., Rothwarf, D. M., Delhase, M., Hayakawa, M., and Karin, M. (1997). Cell 91, 243–252.

Having now fully described the invention, it will be apparent to one of ordinary skill in the art that many changes and modifications can be made thereto without departing from the spirit or scope of the invention as set forth herein.

What is claimed as new and is desired to be secured by Letters Patent of the United Stated is:

1. A purified modulator of NF-κB, which is a peptide comprising SEQ ID NO: 1 and having the following characteristics:
   a) an apparent molecular weight of approximately 48 kD;
   b) a pI of approximately 5.66;
   c) contains a leucine zipper motif; and
   d) binds to a kinase involved in the activation of NF-κB.

2. A composition comprising a pharmaceutically acceptable carrier and the modulator of claim 1.

3. A purified modulator of NF-κB, which is a peptide, wherein the amino acid sequence of the peptide is SEQ ID NO:1.

4. A composition comprising a pharmaceutically acceptable carrier and the modulator of claim 3.

* * * * *